US011348693B2

(12) United States Patent
Joseph et al.

(10) Patent No.: US 11,348,693 B2
(45) Date of Patent: May 31, 2022

(54) GRAPH CONVOLUTION BASED GENE PRIORITIZATION ON HETEROGENEOUS NETWORKS

(71) Applicant: Tata Consultancy Services Limited, Mumbai (IN)

(72) Inventors: Thomas Joseph, Bangalore (IN); Aditya Rao, Bangalore (IN); Naveen Sivadasan, Hyderabad (IN); Saipradeep Govindakrishnan Vangala, Bangalore (IN); Sujatha Kotte, Hyderabad (IN); Rajgopal Srinivasan, Hyderabad (IN)

(73) Assignee: Tata Consultancy Services Limited, Mumbai (IN)

( * ) Notice: Subject to any disclaimer, the term of this patent is extended or adjusted under 35 U.S.C. 154(b) by 309 days.

(21) Appl. No.: 16/378,265

(22) Filed: Apr. 8, 2019

(65) Prior Publication Data
US 2019/0311811 A1    Oct. 10, 2019

(30) Foreign Application Priority Data

Apr. 7, 2018  (IN) .............................. 201821013349

(51) Int. Cl.
*G16H 70/60*    (2018.01)
*G16H 10/20*    (2018.01)
(Continued)

(52) U.S. Cl.
CPC .......... *G16H 70/60* (2018.01); *G06F 16/288* (2019.01); *G06F 16/9024* (2019.01); *G06N 5/04* (2013.01);
(Continued)

(58) Field of Classification Search
CPC .. G06Q 50/22–24; G16H 70/60; G16H 10/20; G06F 16/288; G06F 16/9024;
(Continued)

(56) References Cited

U.S. PATENT DOCUMENTS 8,874,432 B2 * 10/2014 Qi ........................... G06F 40/30
704/9
10,006,148 B2 * 6/2018 Chen ........................ G16B 5/30
(Continued)

OTHER PUBLICATIONS

Davis DA, Chawla NV (2011) Exploring and Exploiting Disease Interactions from Multi-Relational Gene and Phenotype Networks. PLoS One 6(7): e22670. https://doi.org/10.1371/journal.pone.0022670 (Year: 2011).*

(Continued)

*Primary Examiner* — Jason S Tiedeman
*Assistant Examiner* — Jessica Marie Webb
(74) *Attorney, Agent, or Firm* — Finnegan, Henderson, Farabow, Garrett & Dunner, LLP

(57) ABSTRACT

This disclosure relates generally to method and system for graph convolution based gene prioritization on heterogeneous networks. The method includes obtaining a set of entities for human rare diseases from one or more sources containing rare diseases, genes, phenotypes for rare diseases and biological pathways and constructing an initial heterogeneous network using each of an entity from the set of entities. the initial heterogeneous network applying Graph Convolution-based Association Scoring (GCAS) to the initial heterogeneous network to derive inferred associations and creating a Heterogeneous Association Network for Rare Diseases (HANRD) by adding the inferred associations to the initial heterogeneous network and generating a prioritized set of genes for an input query being received in the HANRD.

9 Claims, 8 Drawing Sheets

(51) Int. Cl.

| | |
|---|---|
| *G06F 16/28* | (2019.01) |
| *G06F 16/90* | (2019.01) |
| *G16B 45/00* | (2019.01) |
| *G16B 35/10* | (2019.01) |
| *G16B 50/10* | (2019.01) |
| *G06N 5/04* | (2006.01) |
| *G06F 16/901* | (2019.01) |

(52) U.S. Cl.
CPC .............. *G16B 35/10* (2019.02); *G16B 45/00* (2019.02); *G16B 50/10* (2019.02); *G16H 10/20* (2018.01)

(58) Field of Classification Search
CPC ...... G06F 16/9027; G06N 5/04; G16B 45/00; G16B 35/10; G16B 50/10
See application file for complete search history.

(56) References Cited

U.S. PATENT DOCUMENTS

| | | | | |
|---|---|---|---|---|
| 10,347,359 | B2* | 7/2019 | Dewey | G16B 5/00 |
| 10,366,324 | B2* | 7/2019 | Riley | G06N 3/0454 |
| 10,671,908 | B2* | 6/2020 | Simard | G06K 9/6267 |
| 2004/0093331 | A1* | 5/2004 | Garner | G06N 5/022 |
| 2013/0268290 | A1* | 10/2013 | Jackson | G16H 70/60 705/2 |
| 2014/0046696 | A1* | 2/2014 | Higgins | G16H 50/50 705/3 |
| 2014/0359422 | A1* | 12/2014 | Bassett, Jr. | G16B 20/40 715/230 |
| 2015/0149191 | A1* | 5/2015 | Lee | G06F 40/30 705/2 |
| 2017/0242959 | A1* | 8/2017 | Page | G16B 20/00 |
| 2018/0082197 | A1* | 3/2018 | Aravamudan | G16B 50/10 |
| 2018/0095969 | A1* | 4/2018 | Jung | G16B 20/00 |

OTHER PUBLICATIONS

Kipf, Thomas. Graph Convolutional Networks. Sep. 30, 2016. GitHub. p. 1-6. https://tkipf.github.io/graph-convolutional-networks/ (Year: 2016).*

Kipf TN, Welling M. Semi-supervised classification with graph convolutional networks. ICLR. 2017. all pages. https://arXiv:1609.02907. (Year: 2017).*

Kipf et al. Graph Convolution Network. Sep. 27, 2017. Accessed using Wayback Machine. all pages. https://web.archive.org/web/20170927083127/https://github.com/tkipf/gcn. (Year: 2017).*

Yang H, Robinson P, Wang K. Phenolyzer: phenotype-based prioritization of candidate genes for human diseases. Nat Methods. 2015; 12(9):841-3. all pages. https://www.nature.com/articles/nmeth.3484. (Year: 2015).*

Ullah M, Aono M, Seddiqui M. Estimating a ranked list of human hereditary diseases for clinical phenotypes by using weighted bipartite network. In: Proceedings from the AnnualInternational Conference of the IEEE Engineering in Medicine and Biology Society,Osaka: 2013. p. 3475-8. all pages. (Year: 2015).*

Deng Y, Gao L, Wang B, Guo X. HPOSim: an R package for phenotypic similarity measure and enrichment analysis based on the human phenotype ontology. PloS One. 2014; 10(2):e0115692. all pages. (Year: 2014).*

Kelder T, van Iersel M, Hanspers K, Kutmon M, Conklin B, Evelo C, Pico A. WikiPathways: building research communities on biological pathways. Nucleic Acids Res. 2012; 40(Database issue):D1301-7. all pages. (Year: 2012).*

Mostafavi, S. et al. (Jul. 2010) "Fast integration of heterogeneous data sources for predicting gene function with limited annotation," *Bioinformatics*, vol. 26, issue 14; pp. 1759-1765.

Wang, X. et al. (Sep. 2011) "Network-based methods for human disease gene prediction," *Briefings in Functional Genomics*, vol. 10, issue 5; pp. 280-293.

Zhao, Z-Q. et al. (2015). "Laplacian normalization and random walk on heterogeneous networks for disease-gene prioritization," *Computational Biology and Chemistry*, vol. 57; pp. 21-28.

Mostafavi et al., "Fast integration of heterogeneous data sources for predicting gene function with limited annotation", Bioinformatics, Oxford University Press, vol. 26, Issue 14, pp. 1759-1765, (2010) Link: https://academic.oup.com/bioinformatics/article/26/14/1759/177586.

Wang et al., "Network-based methods for human disease gene prediction", Briefings in Functional Genomics, Oxford University Press, vol. 10, Issue 5, pp. 280-293 (2011) Link: https://academic.oup.com/bfg/article/10/5/280/206849.

Zhao et al., "Laplacian Normalization and Random Walk on Heterogeneous Networks for Disease-gene Prioritization" Computational Biology and Chemistry, Elsevier Ltd., vol. 57, 25 pages, (2015) Link: https://eprints.qut.edu.au/100802/1/LapRWRH_CBC.pdf.

Rao et al., "Phenotype-driven gene prioritization for rare diseases using graph convolution on heterogeneous networks", BMC Medical Genomics, Open Access, vol. 11, Article No. 57, pp. 1-12, (2018) Link: https://bmcmedgenomics.biomedcentral.com/articles/10.1186/s12920-018-0372-8.

Stelzer et al.; "VarElect: the phenotype-based variation prioritizer of the GeneCards Suite" BMC Genomics, Open Access, vol. 2, issue 17. pp. 195-206, (2016) Publisher: https://bmcmedgenomics.biomedcentral.com/articles/10.1186/s12920-018-0372-8.

Smedley et al.; "Phenotype-driven strategies for exome prioritization of human Mendelian disease genes", Genome Medicine, BioMed Central Ltd, vol. 7, Issue 81, (2015) Link: https://genomemedicine.biomedcentral.com/articles/10.1186/s13073-015-0199-2.

Köhler et al.; The Human Phenotype Ontology in 2017, Nucleic Acids Research, Oxford University Press, vol. 45, Issue D1, pp. D865-D876, (2016) Link: https://academic.oup.com/nar/article/45/D1/D865/2574174.

Köhler et al.; "Clinical Diagnostics in Human Genetics with Semantic Similarity Searches in Ontologies" AJHG, The American Society of Human Genetics, vol. 85, Issue 4, pp. 457-464, (2009) Link: https://www.sciencedirect.com/science/article/pii/S0002929709003991.

Yang et al.; "Phenolyzer: phenotype-based prioritization of candidate genes for human diseases", Nature Methods, American Chemical Society, vol. 12, issue 9, pp. 841-843, (2015) Link: https://www.ncbi.nlm.nih.gov/pmc/articles/PMC4718403/.

Godard et al., "PCAN: phenotype consensus analysis to support disease-gene association", BMC Bioinformatics, vol. 17, Issue 518, (2016) Link:https://bmcbioinformatics.biomedcentral.com/track/pdf/10.1186/s12859-016-1401-2.pdf.

James et al.; "A visual and curatorial approach to clinical variant prioritization and disease gene discovery in genome-wide diagnostics", Genome Medicine, Springer Nature Switzerland AG, vol. 8, Issue 13, pp. 1-17, (2016) Link:https://link.springer.com/content/pdf/10.1186/s13073-016-0261-8.pdf.

Smedley et al.; "Next-generation diagnostics and disease-gene discovery with the Exomiser", HHS Author Manuscripts, Nat Protoc, vol. 10, issue 12, pp. 1-12, (2015) Link:https://www.ncbi.nlm.nih.gov/pmc/articles/PMC5467691/.

Antanaviciute et al.; "OVA: integrating molecular and physical phenotype data from multiple biomedical domain ontologies with variant filtering for enhanced variant prioritization", Bioinformatics, vol. 31, issue 33, (2015) Link:https://academic.oup.com/bioinformatics/article/31/23/3822/209474.

Singleton et al.; "Phevor Combines Multiple Biomedical Ontologies for Accurate Identification of Disease-Causing Alleles in Single Individuals and Small Nuclear Families", The American Journal of Human Genetics, vol. 94, Issue 4, pp. 599-610, (2014) Link:https://www.sciencedirect.com/science/article/pii/S0002929714001128.

Sifrim et al.; "eXtasy: variant prioritization by genomic data fusion", Nature Methods, Springer Nature Limited, 11 pages, (2013) Link: https://www.nature.com/articles/nmeth.2656.

Guney et al.; "Exploiting Protein-Protein Interaction Networks for Genome-Wide Disease-Gene Prioritization", PLOS One, vol. 7, Issue 9, pp. 1-12, (2012) Link:https://journals.plos.org/plosone/article?id=10.1371/journal.pone.0043557.

(56) References Cited

OTHER PUBLICATIONS

K P et al.; "A study of gene prioritization algorithms on PPI networks", 2016 International Conference on Advances in Computing, Communications and Informatics (ICACCI), IEEE, pp. 1-17, (2016) Link:https://www.researchgate.net/profile/Bhadrachalam-Chitturi/publication/308389210_A_Study_of_Gene_Prioritization_Algorithms_on_PPI_Networks/links/57e287d008ae1f0b4d95e673/A-Study-of-Gene-Prioritization-Algorithms-on-PPI-Networks.pdf.

Wu et al.; "Network-based global inference of human disease genes", Molecular Systems Biology, EMBO and Nature Publishing Group, vol. 4, Issue 189, pp. 1-11, (2008) Link:https://www.embopress.org/doi/pdf/10.1038/msb.2008.27.

Vanunu et al.; "Associating Genes and Protein Complexes with Disease via Network Propagation", PLoS Computational Biology, vol. 6, Issue 1, pp. 1-9 (2010) Link:https://journals.plos.org/ploscompbiol/article?id=10.1371/journal.pcbi.1000641.

Li et al.; "Genome-wide inferring gene-phenotype relationship by walking on the heterogeneous network", Bioinformatics, Advance Access Publication, vol. 26, Issue 9, pp. 1219-1224, (2010) Link: https://academic.oup.com/bioinformatics/article/26/9/1219/199640?login=true.

Xie et al.; "Reconstructing disease phenome-genome association by bi-random walk", University of Minnesota's Digital Conservancy, Technical Report, TR 13-023, 1 Title page, pp. 1-15 (2013)Link: https://conservancy.umn.edu/bitstream/handle/11299/215926/13-023.pdf?sequence=1.

Ullah et al.; "Estimating a ranked list of human hereditary diseases for clinical phenotypes by using weighted bipartite network", Annual International Conference of the IEEE Engineering in Medicine and Biology, Society (EMBC), 5 pages, (2013) Link: https://www.researchgate.net/publication/257601462_Estimating_a_ranked_list_of_human_hereditary_diseases_for_clinical_phenotypes_by_using_weighted_bipartite_network/link/54d723b20cf2970e4e70553d/download.

Hammond et al.; "Wavelets on graphs via spectral graph theory", Applied and Computational Harmonic Analysis, Elsevier, vol. 30, Issue: 2, pp. 129-150, (2011) Link: https://reader.elsevier.com/reader/sd/pii/S1063520310000552?token=09A3951C737E716E0D67D97C999398F3037F11DF5020921BA84E85FDC4A7A19EB5438B8B29B431D9BD3D0402A62D4686&originRegion=eu-west-1&originCreation=20210713054713.

Kipf et al.; "Semi-supervised classification with graph convolutional networks", Machine Learning, Arxiv, pp. 1-14, (2017) Link: https://reader.elsevier.com/reader/sd/pii/S1063520310000552?token=09A3951C737E716E0D67D97C999398F3037F11DF5020921BA84E85FDC4A7A19EB5438B8B29B431D9BD3D0402A62D4686&originRegion=eu-west-1&originCreation=20210713054713.

Gray et al.; "Genenames.org: the HGNC resources in 2015", Nucleic Acids Research, Oxford Academic, vol. 43, Database issue, pp. D1079-D1085, (2015) Link: https://watermark.silverchair.com/gku1071.pdf?token=AQECAHi208BE49Ooan9kkhW_Ercy7Dm3ZL_9Cf3qfKAc485ysgAAAsEwggK9BgkqhkiG9w0BBwagggKuMIIC qgIBADCCAqMGCSqGSIb3DQEHATAeBglghkgBZQMEAS4wEQQMJF6fBpdbaIVWDEIVAgEQgIICdBkB_GmKc8_HIDw4O_IdGuCQwcm7vXkPnBT01Bxlz4NpLds2O4rHDTMXCX9pbFn_GRVta6A1GFm-eiSIx7XwcLGsxIWcxkeS5CPeOIINsKf5mkvKbbpRjmpvOvTNE6E08FRsgW50w4pdST_j15f2ChxW9CxLIrqS3mOJQDYAcfF_haPCg_YWh87Bft7O0SIJMdXnofXKnyAO7xPxdvRx6zUE_4KOzrhSVPd16Xw_N2547wbvKxQi151sriuY2izuWT_kWeYKE-w7wVLyqn3LIVAGQTYXRkpdn-2_a7JT7YRutoncWovJ3ZkKF-1E-yrjmpG8yodq_7AfA7YWOPOGD54q5yzlaJSXmCcNEswTUS465zzFfJnq7O9d4Yu492k8tlxLF-ITIWaVD-Lk8fECDWCHGyCw96dhnl6pmoluP2sDoot7FkLqXkWS_UJfWIjrcb8DG-yJZ6AhjpBOCcE4vzBHULgMp5zogrLUFVDeIKdir7e3ksZsxVm10S4g24zeNwCvEP_eDYDDZqDOMC555vyn3bSB9N_V-5wTZk3RkcaRFo2YfrGFrE3zrreTHqpSJaFO04lkPsX9SpY1eS4XWVSzoPzij6g3nKPwjLWzcf78HNoLJq_T8FJZBHmzVOulcQ4RIc8T0RPikpywMsj98VHhvWBf6BufPgedD_p4VMFL84cNJgZ_KpdR42Kfm_yX8SdaqC_F5p_V5tloCd5tqrEtbSSL7muzVpfYrWkPMY8XNi1rtY2-q-6S0fAxZRUXR6qUTE54IrENJ379Hokq9AYWYvWLm1xqCbrkyieHsmNOfw7C3hYfmpTAs_Da1hUf3FpavKRY.

Kelder et al.; "WikiPathways: building research communities on biological pathways", Nucleic Acids Research, Oxford Academic, vol. 40, Database issue, pp. D1301-D1307, (2012) Link: https://watermark.silverchair.com/gkr1074.pdf?token=AQECAHi208BE49Ooan9kkhW_Ercy7Dm3ZL_9Cf3qfKAc485ysgAAAsEwggK9BgkqhkiG9w0BBwagggKuMIICqgIBADCCAqMGCSqGSIb3DQEHATAeBglghkgBZQMEAS4wEQQMH-ySRxmfxPG4u3gDAgEQgIICdMA7xVUpBmY8eWwRLetGqVFhNxiLTRp1hBrsoW0Vrac7yheBid7LPL6VnRbeSS9iFLz5GEgJyso1IS5kSI0ITNV-BjNiLrj9sXpGnUjhRzUSo8tSua2fHi28yS9IgZhoxE5mugZS6VruhNzKOMEwvNddDFkFKpZrD1W6iqOiFbwgQ0h77CCDh_kbx6j8hh0xCBHyW4zUsdjcqbhxd61K60z4YTpZoo0e0apPtQbBaE6PeaGL0aqdrGHjRAyJZoEGatqMmH7m8jTRuLnSjPTcQalycAyF53GId-Gm3mZzZSOeKOnu8bTp4xStqivYPHqbOKb288UssQK4qbvKhINWGjAslopHx9WofN1vUKrAix56IFsaV3-iE3woR8AQIYumk42rjUp9KILgiNL9425hau5-e5j12KBhRiEFPR5r0v3fxBMaZuDtWp_ScdieD7oF8ZogWDykPKuba267gS1ar0GHd_7nDo9dk4pSYOiBeWhntHn8m-PLctljwjQRrrQQbSrlmTIuPOOc29yxyKOybXu-wCNDTJF8rf-IOppF2FtgK6Mqc175zkLNU-6N1f_wA4_SZH0-VEpqop2aicrbcpHh8-GYISTneHrAL72IYbri6Zs-EWW477QvoDTpdJP558hEGVEaANr6UUy9CYXDEuBf1XS-tobn0TkD69x1oYs3bw2GP_nyAqBW36XqwLx0fwCHD6K7ufJKdrCSPm2ddHEofOt-VrzrskN9rvonbx4ZeHnF3TLJOJtPXIygDMKhcet7x9w2OINt97HQDCIJbkyAhLIxQoVKgLO0E_1xlkhmdoiZiJurKb1BnRRPqGTh96-7SZjY.

Kutmon et al.; "WikiPathways: capturing the full diversity of pathway knowledge", Nucleic Acids Research, Oxford Academic, vol. 44, Database issue, pp. D488-D494, (2015) Link: https://watermark.silverchair.com/gkv1024.pdf?token=AQECAHi208BE49Ooan9kkhW_Ercy7Dm3ZL_9Cf3qfKAc485ysgAAAsAwggK8BgkqhkiG9w0BBwagggKtMIICqQIBADCCAqIGCSqGSIb3DQEHATAeBglghkgBZQMEAS4wEQQMIKfK4Qj3Kv0O9XoVAgEQgIICc6iJyYCVw4irPUrHIQCieBAg1qZmNfCh6QOb79slttnE6rMOjpNTgkp9F24KyojyKumKLLouE8intVguTQndfnqiAnzYOsEKgtEpAmcDqPw3jLAXoTV9WF1EoRZhOeXDvt5Sg_P6h8pmarHgNuFreV2ebfBmrm3UJI1xAaHdpVqHEI1zDOWtRHn-O11TJ1VH-C8vD3NXXYF0S5St9MEQXNHV_f_BN-Vjuj0qWIYQRjx7xii1MuAJhK96CXj-eLMFsL3JpJ17QWknG_AZVL-ejvc07SskrA9eIG97Z5ihCqMI1iWtFy3EZF7O2kxz6LsqTBwX73OTOg6ayKCauF3RKIZvAj23KUCktoJoK83q4OYPIY25MwNvx7IzjnoCkJmheHXVeWcFpJnmRB04DV4c7k0Fip3EqdqP135Ro-sXHFUAbtZ9uAW0jL7nY2BGM0JNt4JzjDtEjpY5oVwJXzNdf0pP-iFC3oZSMmeIN9TSzGYRN0T5xjXODyTKAjltPZeQ08RbrlA7fm0dHbYAgf61CEtb-Mzp-aYB_IqD5B3Do_M_5uos5BgLn19JDPc8JV3IHSYtw5BCT6MBNVm21Rzknr45F-fazCyI446Np_NCdkm5rSVKgULumrsCxGYXteYs5I8NPnqHPC-K0qcknuTIcVTyaIMM8sUrJ4g_o5wrlw7qFMOSNWM17W_3wiGcqsYJxSMz_69_JwV_mwdvGi5LAQIrL6f6eNGJJUFKS7zyFQWUTpBHj27CGxf6NrXwukM3nABa2BSqRBj6Wa0wOtQIIUT73z2G1cSMo1aKJeQMpZGO6kmuw635kKDtihEfuU4zg8dEJg.

Deng et al.; "HPOSim: an R package for phenotypic similarity measure and enrichment analysis based on the human phenotype ontology", Research Article , PLOS One, pp. 1-12, (2015) Link: https://storage.googleapis.com/plos-corpus-prod/10.1371/journal.pone.0115692/1/pone.0115692.pdf?X-Goog-Algorithm=GOOG4-RSA-SHA256&X-Goog-Credential=wombat-sa%40plos-prod.iam.gserviceaccount.com%2F20210713%2Fauto%2Fstorage%2Fgoog4_request&X-Goog-Date=20210713T053606Z&X-Goog-Expires=86400&X-Goog-SignedHeaders=host&X-Goog-Signature=935d16ed5195f9b019381946b3917cb56bbcbffbf3138b89e0ea15dcc422b1714caf7b0e300ad75988d6f92f5cf06cb077e4b838b53987538ee5081879f0eb6465eda56528f18a719b0a32dddb2f17f9cb40fd19b7e83ac

(56) References Cited

OTHER PUBLICATIONS bd11e0d556b0ea5345bfb491b62601ba3591a841b6b4ece860488ae5b88d373a2d569653ffac480d8a3f96918be68d6529e2db9f4a0133f03c5fbdf639ce0a60d4b8b8c427308d100ee7e0eb98940bae349d52ed4730c376b0fdcf6374f2894ccc3587e4979eb744399d7616c8747ec3dad7170439d13786a6003b47816a408450a4a66de67fc8b49fd4daf0c447c39b4eabccc2af38e7e848ecc78cb8e8e89675d128c037d671a2b.

Hanley et al.; "Title: The meaning and use of the area under a receiver operating characteristic (ROC) curve", Radiology, RSNA, vol. 143, No. 1, pp. 29-36, (1982) Link: https://pubs.rsna.org/doi/pdf/10.1148/radiology.143.1.7063747.

Bone et al.; "Computational evaluation of exome sequence data using human and model organism phenotypes improves diagnostic efficiency", Genetics in Medicine, Nature, vol. 18, No. 6, pp. 608-617, (2016) Link: https://www.nature.com/articles/gim2015137.pdf.

Lee et al.; "Clinical exome sequencing for genetic identification of rare Mendelian disorders", American Medical Association, Jama Network, vol. 312, Issue 18, pp. 1880-1887, (2014) Link: https://www.semanticscholar.org/paper/Clinical-exome-sequencing-for-genetic-of-rare-Lee-Deignan/8b04738a5e322ef60992ba82eef531b4f1ded950.

Vasant et al. "ORDO: An ontology connecting rare disease, epidemiology and genetic data" Bio-Ontology, Research Gate, 1 Title Page, pp. 1-5, (2014) Link: https://www.researchgate.net/publication/281824026_ORDO_An_Ontology_Connecting_Rare_Disease_Epidemiology_and_Genetic_Data/link/55f99bc408aeafc8ac266edf/download.

Gene Ontology Consortium, "Gene Ontology Consortium: going forward", Nucleic Acids Research, Oxford Academic, vol. 43, Database issue, pp. D1049-D1056, (2014) Link: https://watermark.silverchair.com/gku1179.pdf?token=AQECAHi208BE49Ooan9kkhW_Ercy7Dm3ZL_9Cf3qfKAc485ysgAAAsEwggK9BgkqhkiG9w0BBwagggKuMIICqgIBADCCAqMGCSqGSIb3DQEHATAeBglghkgBZQMEAS4wEQQMrVE1j8a_LfWivLhAgEQgIICdNwHpogXAbEeU_ydLwmC8b5L4uQE11w_LxTic9YzJDmu1LJHRGq_0WIdKHUpfhMx0-cuCGSVF53GQmH_orSMQZv1P9aQfFRu5EFnKmzETMrPvDAj6LnWSF2dEXDSAagYAEp9vybPUwOeeDWI2HDgZvA8bRCyCIrdaKQ3MGdwUopE_HFrvJzyQ09cmxPHowF1nAToeo9X8I5PkEa6jMn6A79xSLEKWrG1HXoVvEh0IB31e0M0IzcJ4kGJ4dWogsaNyrBQe6bMsnW-hAQcRAV_drQStu7_nhBBp4Sru3STqjXSuQ7-_JNahYN2Hoj1nuQcrPAY2WdEwTNaBxfTypeDnjaxt11sd_HTLhydBHXjvmF6OXJ5ImZrY0I7Ie-nHDPDZkobZNNgOmZ8Jd-v2YQhIhbLYSfjo0b1c86SuXh8B_Ivn1LiBzAqtZGgphcez5-Ots4OeMoLuah-t-N3oogoSmarHp75ygHFdDKIMw2kndc4hJMMfW7CwCgMxaWbNj1jLvoKjCWBLniqn3TUTMnCTRUSz9S6PAs-Y1q74fIcHFqI1aGEitv2iR6js6NyfYEXfyUNTy4wkapLeSHwvUhzNnasvtofH4Fom_GozmASdrpFJebLtqGvg49ANgfXI_z5uentNn2I6ocvAJLheMW_Y18_5ajqxDiwjKrSOF6_AFIsWhyALaiRVNrFiTwU5dSb2FPPglnjB9w0cyVPFSSDCIDzDIO8AvIAYLyWhjxfjTkGqWMLPHI1JdYtVkYygFQKMHf7QcmlxD_9yLZo_DbSadhcTg24BS7ZF1n7HfD4ZQacuLakhac9VPwLcbnFp1zsslzBoMA.

Piñero et al.; "DisGeNET: a discovery platform for the dynamical exploration of human diseases and their genes", Database, Oxford University Press, pp. 1-17, (2015) Link: https://watermark.silverchair.com/bav028.pdf?token=AQECAHi208BE49Ooan9kkhW_Ercy7Dm3ZL_9Cf3qfKAc485ysgAAAt0wggLZBgkqhkiG9w0BBwagggLKMIICxgIBADCCAr8GCSqGSIb3DQEHATAeBglghkgBZQMEAS4wEQQMm17v_dYQB7ZDK2q9AgEQgIICkFM2_tIGF-WGQMG-5f3P6KD6qM-qmh2AQRSZFfCLfVZdGv5xocxN5HTZOFQGPW8P5a52BOSEG0ZpRNLSzKZk5CSOWeCqrrda9AIQHRD6Bg7yei4wPJvzmWDNNFvPukYMEI0c27z0GoQwg8DPY75fnGzs8272br8L-IP6TaEoEfQIKnee1xM9WsC5R98LybIBSbLpQGZNceIA_hCex1N5pgOm8iBn2IRt4VVIOXXVsWGpcyLqSUWooEkT8oWXUkb-4mL4yeXjsDP0JkQZOszcLRCyNne6zIL7ZmHr7Z5JSJnQ5gJvMA9SdCk2IPxmEq7TBVsgL1SSX8sKZRWuWSfYxd80bFKDHuzD96QEbmmoRF6ZRe5aPIn0IfK_Hz1a-08H-6pxCozzUKItrWbzPgRYFoJXgMFz16TINaXN2K_82xnKGrjM3BsogtEtfF16kqt0RCj2HXuASDmYxwmBDDTfdG2GdA2vs6G-XwuYPnp80dMJjOJP7Yy3ggvmEmSQ_5nOhU1HgOSCbrLpj28Pv4JG0KdZq8TFbz104FJYKxPQ1vT3-LV6exdgzn4irJoDHsQ0u45ERv4aFOaAD6dfQSb1EtqnyH-KFFthojYv707XsevvXtret8zKQh737Qt2sfdVpI8cSDnsVR1opxp5J8bkpUsgSKRF8w0LKyUq5jjEXC6_nLZVb5fLRmHSyF6BKTixOApqb2q7_108qBOoQF754zfILxVupMtengLI6eIEgdmx-rudjDA5ugMvgi8ox660fJZPkLjcCtT8nbZ4JIFou9uf5HqFx4ZfUF8j_gy9Y-0MTzzluHfbRckDn-4ANcsBYY40CPjoRQauvvHz_tq-OV64-u63rfFzm0B7hCs6cSb-.

Kumar etal.; "Predicting the effects of coding non-synonymous variants on protein function using the SIFT algorithm", Nature Protocols, vol. 4, No. 8, pp. 1073-1081, (2009) Link: https://www.researchgate.net/publication/26325685_Predicting_the_effects_of_coding_non-Synonymous_variants_on_protein_function_using_the_SIFT_algorithm/link/55376dd60cf268fd00189ce9/download.

Author: Adzhubei et a., "A method and server for predicting damaging missense mutations, Nature Methods", Nature, vol. 7, issue 4, pp. 1-5, (2010), Nature Link: http://europepmc.org/backend/ptpmcrender.fcgi?accid=PMC2855889&blobtype=pdf.

* cited by examiner

GRAPH CONVOLUTION BASED GENE PRIORITIZATION ON HETEROGENEOUS NETWORKS

PRIORITY CLAIM

This application is related and claims the benefit of Indian Provisional Patent Application No. 201821013349, filed on Apr. 7, 2018, the entirety of which is incorporated herein by reference.

TECHNICAL FIELD

The disclosure herein generally relates to gene prioritization, and, more particularly, to graph convolution based gene prioritization on heterogeneous networks.

BACKGROUND

One of the major goals of genomic medicine is the identification of causal genomic variants in a patient and their relation to the observed clinical phenotypes. Prioritizing the genomic variants by considering only the genotype information usually identifies a few hundred potential variants. Narrowing it down further to find the causal disease genes and relating them to the observed clinical phenotypes remains a significant challenge, especially for rare diseases.

The success of genomic medicine is crucially dependent on rapid, comprehensive and accurate assessment of a patients genomic variants and the relation of these variants with the observed clinical phenotypes. Variant prioritization identifies a few hundred variants by considering the genotype. Narrowing the variant list further down to and the genes harboring these variants that are responsible for the observed clinical phenotypes remains a significant challenge. This is particularly challenging in the context rare Mendelian genetic diseases. Availability of comprehensive and precise phenotypic data of the patient can significantly aid in solving this problem.

SUMMARY

Embodiments of the present disclosure present technological improvements as solutions to one or more of the above-mentioned technical problems recognized by the inventors in conventional systems. For example, in one embodiment, a processor implemented method for graph convolution based gene prioritization on heterogeneous networks is provided. The method includes obtaining a set of entities for human rare diseases from one or more sources, the set of entities comprising rare diseases, genes, phenotypes for rare diseases and biological pathways. Further includes constructing an initial heterogeneous network using each of an entity from the set of entities as a node and associations between a plurality of entity pairs as symmetric weighted edges forming pair-wise ontological associations and curated associations. Further includes applying Graph Convolution-based Association Scoring (GCAS) to the initial heterogeneous network for deriving inferred associations for the plurality of entity pairs, wherein deriving the inferred associations comprises determining pair-wise association score matrix based on convolution parameters graph convolution associated with each of the entity in the initial heterogeneous network. Further includes creating a Heterogeneous Association Network for Rare Diseases (HANRD) by adding the inferred associations to the initial heterogeneous network and generating a prioritized set of genes for an input query being received in the HANRD, the input query comprising a plurality of phenotypes corresponding to a clinical case, and wherein generating the prioritized set of genes comprises sorting cumulative association score between each of the phenotype from the plurality of phenotypes and associated genes for each of the phenotype in the HANRD.

In another embodiment, a system for graph convolution based gene prioritization on heterogeneous networks is provided. The system includes a memory storing instructions, one or more communication interfaces and one or more hardware processors coupled to the memory via the one or more communication interfaces. The one or more hardware processors are configured by the instructions to obtain a set of entities for human rare diseases from one or more sources, the set of entities comprising rare diseases, genes, phenotypes for rare diseases and biological pathways, construct an initial heterogeneous network using each of an entity from the set of entities as a node and associations between a plurality of entity pairs as symmetric weighted edges forming pair-wise ontological associations and curated associations, apply Graph Convolution-based Association Scoring (GCAS) to the initial heterogeneous network to derive inferred associations for the plurality of entity pairs, wherein deriving the inferred associations comprises determining pair-wise association score matrix based on convolution parameters in graph convolution associated with each of the entity in the initial heterogeneous network, create a Heterogeneous Association Network for Rare Diseases (HANRD) by adding the inferred associations to the initial heterogeneous network; and generate a prioritized set of genes for an input query being received in the HANRD, the input query comprising a plurality of phenotypes corresponding to a clinical case, and wherein generating the prioritized set of genes comprises sorting cumulative association score between each of the phenotype from the plurality of phenotypes and associated genes for each of the phenotype in the HANRD.

In yet another embodiment, one or more non-transitory machine readable information storage mediums are provided. Said one or more non-transitory machine readable information storage mediums comprises one or more instructions which when executed by one or more hardware processors causes obtaining a set of entities for human rare diseases from one or more sources, the set of entities comprising rare diseases, genes, phenotypes for rare diseases and biological pathways. Further includes constructing an initial heterogeneous network using each of an entity from the set of entities as a node and associations between a plurality of entity pairs as symmetric weighted edges forming pair-wise ontological associations and curated associations. Further includes applying Graph Convolution-based Association Scoring (GCAS) to the initial heterogeneous network for deriving inferred associations for the plurality of entity pairs, wherein deriving the inferred associations comprises determining pair-wise association score matrix based on convolution parameters graph convolution associated with each of the entity in the initial heterogeneous network. Further includes creating a Heterogeneous Association Network for Rare Diseases (HANRD) by adding the inferred associations to the initial heterogeneous network and generating a prioritized set of genes for an input query being received in the HANRD, the input query comprising a plurality of phenotypes corresponding to a clinical case, and wherein generating the prioritized set of genes comprises sorting cumulative association score between each of the phenotype from the plurality of phenotypes and associated genes for each of the phenotype in the HANRD.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
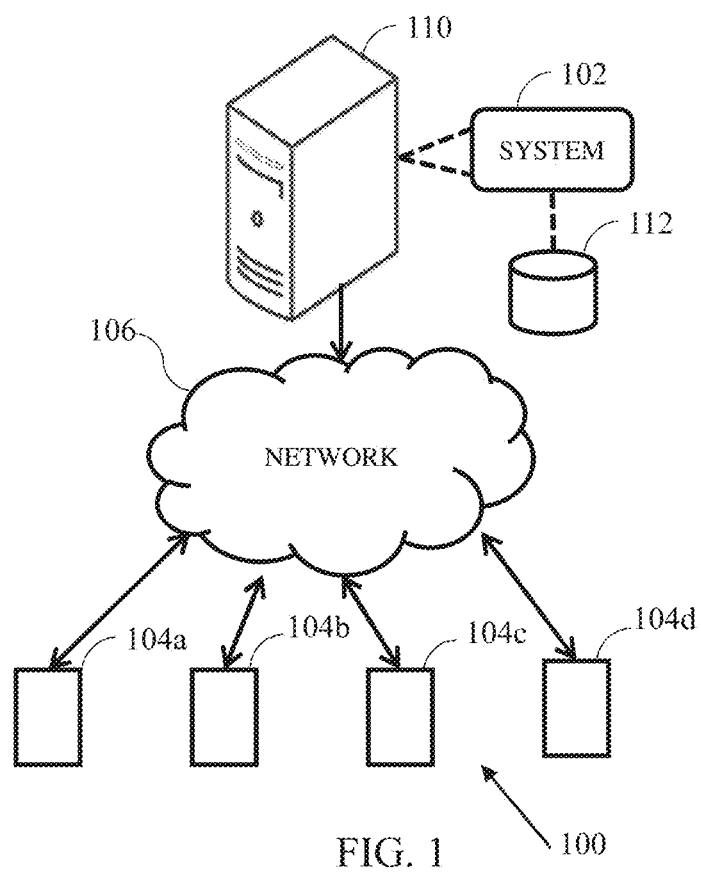
FIG. 1 illustrates an exemplary block diagram of a system for graph convolution based gene prioritization on heterogeneous networks according to an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the claims (when included in the specification).

As known in the literature, one of the major goals of computational deep phenotyping is to aid the analysis of genomic data for personalized genomic medicine. There are existing tools for analysis of genomic data include Phenomizer (e.g., clinical diagnostic in human genetics), Phenolyzer (phenotype-based prioritization of candidate genes for human disease) and PCAN (phenotype consensus analysis to support disease-gene association), amongst others. There also exist composite gene and variant prioritization tools that combine phenotype analysis and variant analysis identified by Whole Exome Sequencing (WES) or Whole Genome Sequencing (WGS) for the study of human disease. The tools available in the art include OMIM Explorer, VarElect, Exomiser, OVA, Phevor, Phen-Gen, eXtasy and Phenotype-Driven Ranking (PDR) algorithm in Ingenuity Variant Analysis. Researchers have reviewed many of these tools. These tools often require as input a set of genes known as 'seed genes' that are already known to be associated with specific phenotypes (e.g., as disclosed in one of the tool OVA). This cause a major limitation when dealing with novel associations between phenotypes and genes. Tools that can infer phenotype-genotype associations when presented with a set of input phenotypes are better placed to overcome this limitation.

On other hand, Phenomizer relies on a semantic network between phenotypic terms to and potential candidate diseases and corresponding genes when presented with a set of input phenotypes. Similar network-based approaches such as GeneMANIA prediction server in biological network integration for gene prioritization and predicting gene function, and GUILD require (1) a network of known associations between various biological entities such as genes and phenotypes, and (2) an algorithm for inferring and scoring associations using the underlying network. The associations could be ontological associations, biological interactions, or 'associations by guilt' where the participating entities co-occur in some context Algorithms for inferring and scoring associations include CIPHER PRINCE, Random walk with restart on heterogeneous network (RWRH) (Bi-Random Walk (BiRW) and MAXimum Information Flow (MAXIF). CIPHER connects protein interaction networks and the phenotype network to try and predict disease genes. PRINCE uses label propagation on networks for association scoring. The RWRH algorithm, when applied to gene prioritization, ranks genes and phenotypes simultaneously in a network built using phenotype-gene associations from the Online Mendelian Inheritance in Man (OMIM) catalog. BiRW computes novel phenotype-gene associations by exploring special sub-graph structures called circular bigraphs in the underlying network. A circular bigraph is defined in BiRW as consisting of a phenotype only path and a gene only path whose endpoints are connected by phenotype-gene links. These structures capture the biological intuition that a new phenotype-gene link would ideally be present in the current network as a path comprising of a phenotype subpath followed by a gene subpath. The phenotype subpath captures the ontological relations and gene subpath captures a sequence of known gene-gene associations. MAXIF uses network flow for association scoring. BiRW has been shown to outperform other network-based algorithms such as PRINCE, CIPHER and RWRH (e.g., refer BiRW).

Identifying causal genes that best explain a set of clinical phenotypes using network-based prioritization approaches remains a challenging task, especially for rare diseases.

Various embodiments of the present disclosure provided systems and methods for graph convolution based gene prioritization on heterogeneous networks. In other words, the present disclosure proposes a phenotype-driven gene prioritization approach using heterogeneous networks in the context of rare diseases.

Embodiments the present disclosure describe the construction of a heterogeneous network including a set of entities such as genes, phenotypes, diseases and pathways as nodes while associations between a set of entities are represented as weighted edges. The weight of an edge represents the score of the association between the entity pairs. Existing association networks usually view ontological associations as distinct from the network of other heterogeneous associations. The systems and methods first build a heterogeneous network consisting of ontological associations as well as curated associations involving genes, diseases, phenotypes and pathways from multiple sources. Motivated by the recent progress in spectral graph convolutions, the systems and methods of the present disclosure implement a graph convolution based technique to infer new phenotype-gene associations from this initial set of associations. These inferred associations were included in the initial network and termed as integrated network HANRD (Heterogeneous Association Network for Rare Diseases). 230 recently published rare disease clinical cases were validated using the case phenotypes as input.

A detailed description of the above described system and method for graph convolution based gene prioritization on heterogeneous networks is shown with respect to illustrations represented with reference to FIGS. 1 through 8.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Referring now to the drawings, and more particularly to FIG. 1 through 8, where similar reference characters denote corresponding features consistently throughout the figures, there are shown preferred embodiments and these embodiments are described in the context of the following exemplary system and/or method.

Figure 2:
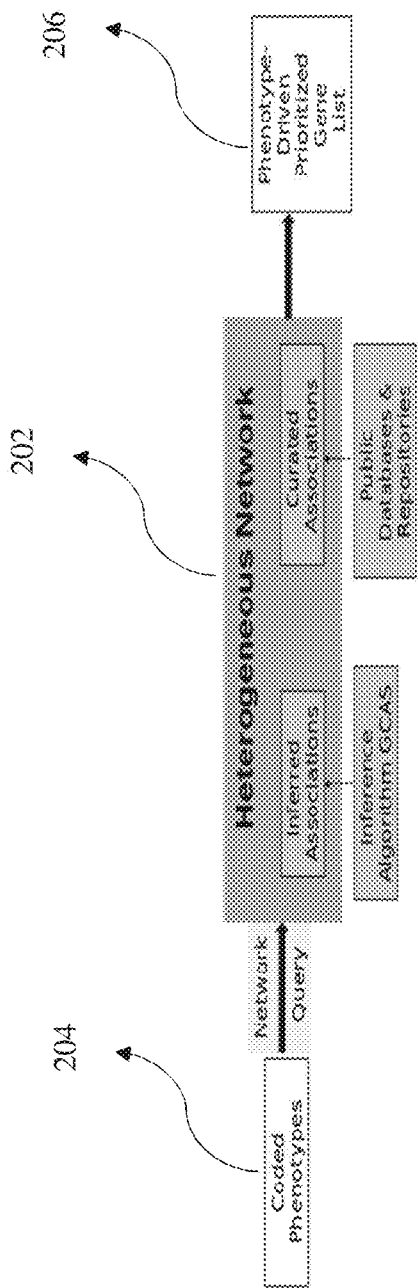
FIG. 2 depicts a block diagram illustrating a functional flow for Phenotype-driven gene prioritization using the system of FIG. 1 in accordance with some embodiments of the present disclosure.

FIG. 1 illustrates a network environment 100 implementing a system 102 for graph convolution based gene prioritization on heterogeneous networks, according to an embodiment of the present subject matter. In one example embodiment, the system 102 is capable of gene prioritization, in particular, developing an information propagation algorithm GCAS (Graph Convolution-based Association Scoring) that performs information propagation on the initial ontological and curated association network and infers novel binary associations between the entities of the network. An important contribution of the disclosed embodiments is that the embodiments provides The present disclosure enables building the HANRD to solve the specific problem of phenotype-driven rare disease gene prioritization wherein the input is a set of phenotypes from clinical cases and the output a ranked list of possible causal genes, the HANRD is as shown in FIG. 2.

Herein, the system 102 may capture an input query, for example, queries via multiple devices and/or machines 104-1, 104-2 . . . 104-N, collectively referred to as devices 104 hereinafter. Examples of the devices 104 may include, but are not limited to, a portable computer, a personal digital assistant, a handheld device, VR camera embodying devices, storage devices equipped to capture and store the images/videos, and so on. In an embodiment, the devices 104 may include devices capable of obtaining information from one or more sources and of receiving an input query comprising a plurality of phenotypes corresponding to a clinical case. The devices 104 are communicatively coupled to the system 102 through a network 106, and may be capable of transmitting the obtained information from one or more sources to the system 102.

In one implementation, the network 106 may be a wireless network, a wired network or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

The devices 104 may send the information associated with rare disease, gene, phenotypes and biological pathways to the system 102 via the network 106. The system 102 is caused to gene prioritization of rare disease on heterogeneous network for an input including a plurality of phenotypes from clinical cases and the output a ranked list of possible causal genes. In an embodiment, the system 102 may be embodied in a computing device 110. Examples of the computing device 110 may include, but are not limited to, a desktop personal computer (PC), a notebook, a laptop, a portable computer, a smart phone, a tablet, and the like. The system 102 may also be associated with a data repository 112 to store the media stream and/or images. Additionally or alternatively, the data repository 112 may be configured to store data from one or more sources and/or information generated during gene prioritization. The repository 112 may be configured outside and communicably coupled to the computing device 110 embodying the system 102. Alternatively, the data repository 112 may be configured within the system 102.

In an embodiment, the system 102 includes an initial heterogeneous network containing pair-wise ontological associations and curated associations and applying Graph Convolution-based Association Scoring (GCAS) to the initial heterogeneous network. The disclosed system 102 enables generating an inferred associations for building HANRD and prioritizing set of genes for an input query including a plurality of phenotypes corresponding to a clinical case on HANRD. The prioritized set of genes is generated by sorting cumulative association score between each of the phenotype from the plurality of phenotypes and associated genes for each of the phenotype in the HANRD. An example representation of the construction of HANRD using the curated associations, ontological association and inferred association using the system 102 is shown and described further with reference to FIG. 3.

Referring to FIG. 2, a heterogeneous network 202 is constructed using curated associations as well as inferred associations from the application of the spectral graph convolution algorithm termed as the GCAS. The constructed heterogeneous network, HANRD 202 is then queried using input phenotypes 204 from individual clinical cases and obtain an output prioritized list of genes 206. Herein, it will be understood that the curated associations are developed using known cases from public databases and repositories. In an embodiment, the set of entities and the associated information are also obtained from the one or more sources, namely, the public databases and repositories. As is seen from FIG. 2, upon processing by the system 102, the constructed network is queried using input phenotypes from individual clinical cases and a prioritized list of genes is obtained as output. Herein, it will be noted that the embodiments herein have been explained by considering for an example embodiments.

In an embodiment, the system 102 may be caused to gene prioritization on heterogeneous network for a plurality of phenotypes corresponding to a clinical case. An example flow-diagram illustrating method for graph convolution based gene prioritization on heterogeneous networks is described in detail with reference to FIG. 4. Although the present subject matter is explained considering that the system 102 is implemented for constructing a heterogeneous network by applying graphs convolution network, it may be understood that the system 102 may is not restricted to any particular machine or environment. The system 102 can be utilized for a variety of domains where graph convolution based gene prioritization is involved. The system 102 may be implemented in a variety of computing systems, such as a laptop computer, a desktop computer, a notebook, a workstation, a mainframe computer, a server, a network server, and the like.

Figure 3:
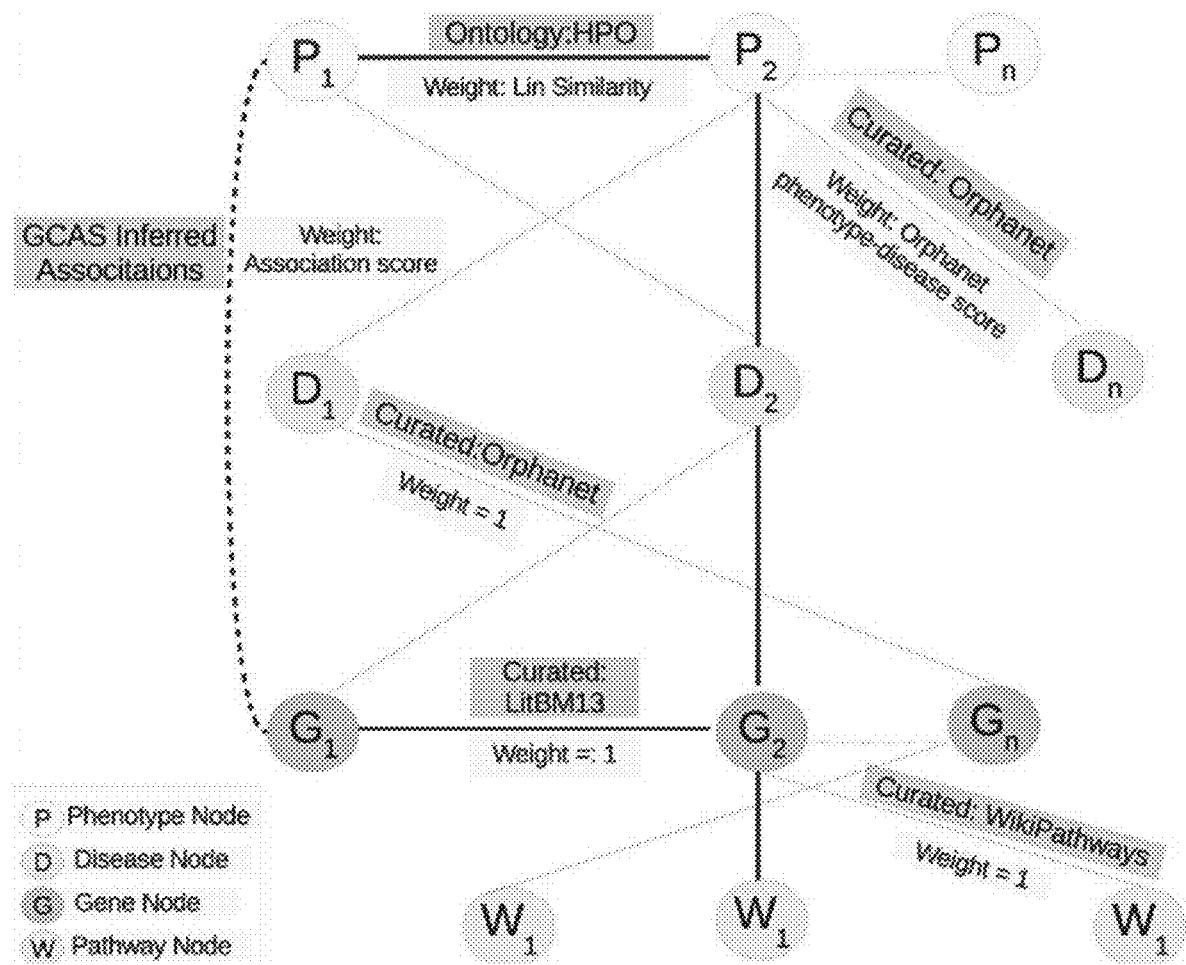
FIG. 3 depicts a representation of various curated and ontological association types in HANRD in accordance with some embodiments of the present disclosure.
Figure 4:
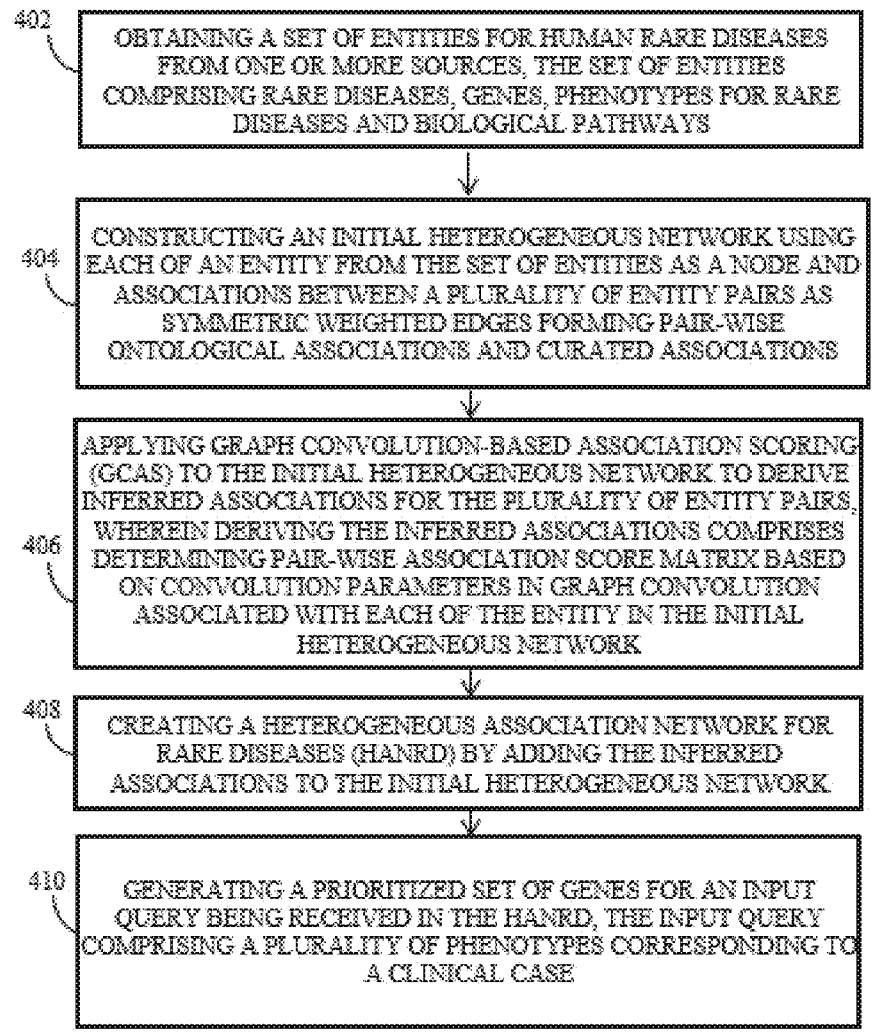
FIG. 4 is a flow diagram illustrating a method for graph convolution based gene prioritization on heterogeneous networks in accordance with some embodiments of the present disclosure.
Figure 8:
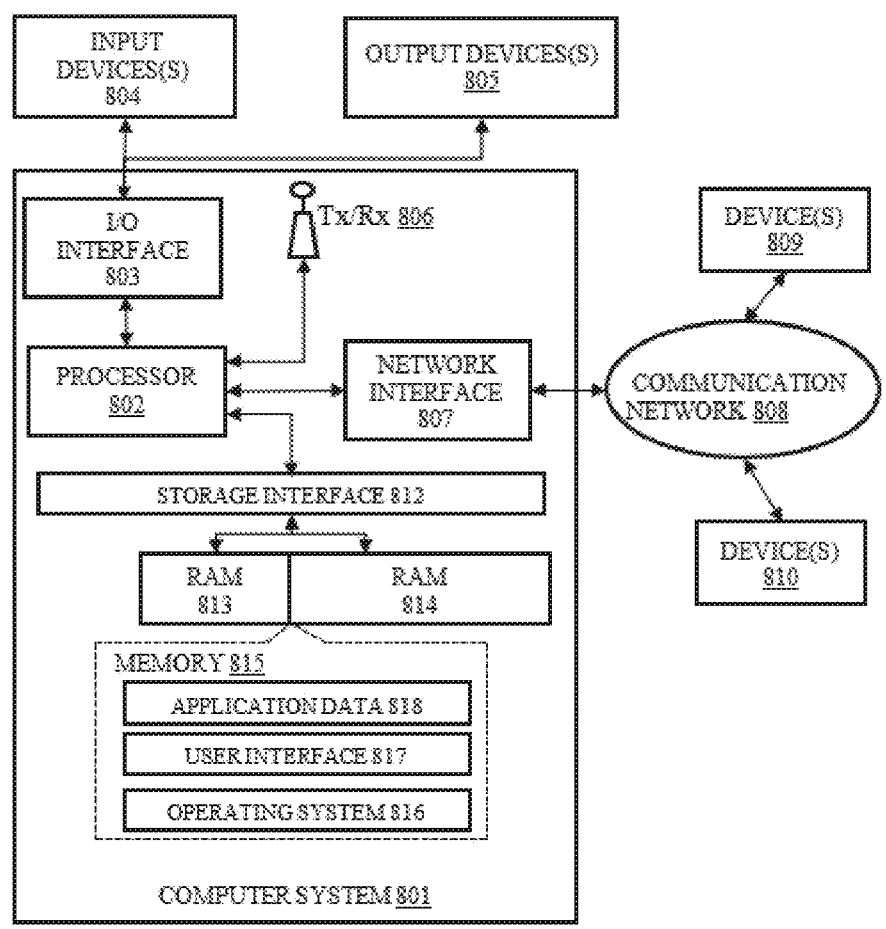
FIG. 8 illustrates a block diagram of a system for graph convolution based gene prioritization on heterogeneous networks in accordance with some embodiments of the present disclosure.

Referring now to FIG. 4, a flow-diagram of a method 400 for graph convolution based gene prioritization on heterogeneous network is described, according to some embodiments of present disclosure. The method 400 may be described in the general context of computer executable instructions. Generally, computer executable instructions can include routines, programs, objects, components, data structures, procedures, modules, functions, etc., that perform particular functions or implement particular abstract data types. The method 400 may also be practiced in a distributed computing environment where functions are performed by remote processing devices that are linked through a communication network. The order in which the method 400 is described is not intended to be construed as a limitation, and any number of the described method blocks can be combined in any order to implement the method 400, or an alternative method. Furthermore, the method 400 can be implemented in any suitable hardware, software, firmware, or combination thereof. In an embodiment, the method 400 depicted in the flow chart may be executed by a system, for example, the system 102 of FIG. 1. In an example embodiment, the system 102 may be embodied in an exemplary computer system, for example computer system 801 (FIG. 8). The method 400 of FIG. 4 will be explained in more detail below with reference to FIGS. 1-3.

Referring to FIG. 4, in the illustrated embodiment, the method 400 is initiated at 402 where the method includes obtaining a set of entities for human rare diseases from one or more sources. The set of entities includes rare diseases, genes, phenotypes for rare diseases and biological pathways. Herein, the one or more sources may include but are not limited to Medical Subject Headings (MeSH), Orphanet, Human Phenotype Ontology (HPO), HUGO Gene Nomenclature Committee and Wiki Pathways. For example, the disease entity is derived from the one or more sources, wherein the disease entity is derived from an Orphanet record including rare disease name and synonyms, descriptions of the rare disease, phenotypes, association strength, genes of the rare disease and MeSH mappings associated with the rare disease. In an example embodiment, Human Phenotype Ontology (HPO) was the primary source for phenotypes. The HPO names and synonyms are augmented with additional synonyms from MeSH (Medical Subject Headings) through MeSH xrefs provided by HPO and HPO-UMLS mappings. Further, Orphanet is used as the primary source for diseases. For example, each Orphanet record contains the rare disease name, synonyms, descriptions, associated phenotypes (including association strength), associated genes as well as MeSH mappings. Also, additional disease synonyms are obtained through MeSH mappings, wherever provided by Orphanet. Furthermore, gene names are derived from HUGO Gene Nomenclature Committee (HGNC) and names of biological pathways is extracted from Wiki® Pathways. The set of entities containing phenotype, rare disease, gene and biological pathway terms is represented as nodes in the initial heterogeneous network. The main term (entity) is propagated as node label, while other terms (entity's synonyms) is represented as synonym obtained from the sources as described above.

At 404, the method includes constructing an initial heterogeneous network using each of an entity from the set of entities as a node and associations between a plurality of entity pairs as symmetric weighted edges forming pair-wise ontological associations and curated associations. The initial heterogeneous network is constructed using curated associations and pair-wise ontological associations, for example as shown in functional flow of FIG. 2. In an example embodiment, the curated associations include disease-gene associations, gene-gene associations, phenotype-disease associations formed using the weights assigned to each of the plurality of pair edges from the one or more sources. The associations between the above nodes are represented by undirected edges with non-negative edge weights (as shown in FIG. 3). In an example embodiment, rare disease data is extracted from Orphanet for building phenotype-disease edges. The weights are calculated and assigned based on defined frequency qualifiers from the Orphanet. The defined frequency qualifiers include "obligate", "very frequent" and "frequent", in one example embodiment. Herein, the defined frequency qualifiers are based on their occurrence in association with the disease. Further, the Orphanet data is also used as source for disease-gene pair. In said example, edge weights for disease-gene pair is set to 1. Furthermore, a high-quality curated interaction dataset known in the art as Lit-BM-13 is used as source for gene-gene associations. In said example, corresponding edges is assigned a weight of 1. Furthermore, Wiki Pathways is used for forming pathway association. Herein, every gene in a pathway is linked to the corresponding pathway node with an edge weight of 1. FIG. 3, with reference to FIG. 1-2, depicts a representation of various curated and ontological association types in HANRD according to an embodiment of the present disclosure.

At 406, the method includes applying Graph Convolution-based Association Scoring (GCAS) to the initial heterogeneous network to derive inferred associations for the plurality of entity pairs. Referring to FIG. 3, it shows various curated, ontological and inferred association types in the HANRD. The HANRD edges may be between phenotypes, diseases, genes and biological pathways. As shown in FIG. 3 and in an example embodiment, the edges are undirected and weighted, and herein the dotted lines indicate the inferred edges, along with each edge type. The weight assignment scheme and the information source between entity nodes along with the curated information is also shown in FIG. 3.

Also, apart from the aforementioned associations weights phenotype-phenotype edges constructed from the HPO is calculated using the standard Lin similarity score for ontological associations. For example, a Lin similarity score of $s(p_1, p_2)$ between two phenotypes, namely, $p_1$ and $p_2$ is given by $2IC(p')/(IC(p_1)+IC(p_2))$, where p' is the most specific common ancestor of $p_1$ and $p_2$ in the ontology hierarchy while IC(p) is the information content of phenotype p, where $$IC(p) = -\ln\left(\frac{f(p)}{N}\right)$$

is used, wherein f(p) is the frequency of p and its descendants in a corpus and N being the total frequency.

The inferred associations are derived by determining pair-wise association score matrix based on convolution parameters in graph convolution associated with each of the entity in the initial heterogeneous network. The method of determining inferred associations further includes applying graph convolution to determine information propagated between neighborhood nodes of each of the plurality of entity pairs in the initial heterogeneous network using the curated associations and based on the convolution parameters comprising convolution operation (C), dampening factor (θ) and convolution depth (K). Further, for each of the plurality of entity pairs having no direct links association scores is determined based on the information propagated to obtain the pairwise association score matrix. Thereafter, inferring associations between each of the plurality of entities are determined based on the pairwise association score matrix to obtain the inferred associations.

Herein, the GCAS of the present embodiments uses graph convolution to propagate information between entity pairs in a network and use the propagated information (information propagation model) to determine association scores between the plurality of entity pairs having no direct links. For GCAS, the initial curated network is assumed to be static and given as input. Herein, propagate information refers to how much information can be allowed to flow or restricted between two nodes in the network based on convolution parameters, namely, convolution operation (C), dampening factor (θ) and convolution depth (K). The mathematical description of GCAS is provided by way of example expression illustrated below:

For example, propagation of a signal $x \in \mathbb{R}^n$ on a given network G consisting of n nodes may be viewed as the convolution of x with a filter g on the network G. Considering $A_{n \times n}$ as an adjacency matrix of G and L to be a normalized graph Laplacian of G given by the equation as follows:

$$L = I_n - D^{-\frac{1}{2}} A D^{-\frac{1}{2}} = U \wedge U^T$$

where $I_n$ is the identity matrix, D is the diagonal degree matrix with $D_{ii}=\Sigma_j A_{ij}$, U is the matrix of eigen vectors of L and $\wedge$ is the diagonal matrix of eigen values of L. Spectral convolution of x with the filter g on the network G can be equivalently represented as $g_\theta * x = U g_\theta U^T x$, where $U^T x$ is the graph Fourier transform of x and $g_\theta = \text{diag}(\theta)$ is a diagonal matrix corresponding to $\theta \in \mathbb{R}^n$, which is the graph Fourier transform of the filter g. Here, $g_\theta U^T x$ gives pointwise multiplication of the Fourier transform of g and x. Further, multiplication of U with $g_\theta U^T x$ in $g_\theta * x$ gives the Fourier inverse for graph Fourier transforms (as derived from one of the known techniques in the literature. Herein, the focus of present embodiments is to design the filter $g_\theta$ that achieves the desired signal propagation on G.

In accordance with an example embodiment, for handling the computational overhead and numerical instabilities, a first order approximation of $g_\theta * x$ based on Chebyshev polynomial approximation of $g_\theta$ is used based on one of one known techniques available in the art. Now, based on the approximation, following representation is given:

$$g_\theta * x \approx \hat{A} x,$$

where $\theta \in \mathbb{R}$ is a single parameter, $$\hat{A} = \tilde{D}^{-\frac{1}{2}} \tilde{A} \tilde{D}^{-\frac{1}{2}},$$

$\tilde{A}=A+I_n$ and $\tilde{D}$ is a diagonal matrix with $\tilde{D}_{ii}=\Sigma_j \tilde{A}_{ij}$. In said example embodiment, for inferring associations the approximation of the convolution operation is used and the information propagated to the $t^{th}$ order neighborhood of the network nodes by performing t consecutive applications of this convolution operation is computed. In the convolution operation, more information may be propagated between two nodes if the path connecting these nodes is stronger (i.e., wider path). After t consecutive convolutions, the resulting values at the network nodes is given by the vector as follows:

$$C_t(x)=\theta' \hat{A}^t x$$

where $\theta'=\Pi_{i=1}^t \theta_i$, and $\theta_i$ is a parameter for the ith convolution. The information propagation model as described above is used to fix $\theta_i=\theta$ for all i>2 where θ is a parameter and another parameter K is used that bounds the convolution depth to compute the final pairwise association score matrix S as depicted below by way of example expression:

$$S = \sum_{t=1}^{K} C_t(I_n)$$

where $C_t(I_n)=\theta^{t-2} \hat{A}^t I_n$ for $t \geq 2$ and $C_1(I_n)=\hat{A}(I_n)$. The present disclosure considers only the off-diagonal entries of matrix S. Herein, the key parameters of the technique are thus K and θ. Parameter K restricts the inferred associated to entity pairs that are at most K links away in the initial heterogeneous network. The parameter $\theta \in [0,1]$ can be understood as the damping or penalizing factor that dampens information flow along longer paths. The damping increases by a multiplication θ for every additional link in path. By choosing $\theta^{t-2}$ as the parameter in $C_t(I_n)$, the damping is applied only for information flow along paths having three or more links. The method of arriving at the inferred association using graph convolution is referred as the GCAS (Graph Convolution-based Association Scoring).

In an example embodiment, values for parameters K and θ were selected by performing a grid search across a range of values in K and θ. For each combination of K and θ values, the GCAS was run/executed on multiple random sub-networks of the original network and its performance for inferring missing associations in the sub-network is analyzed. In said example embodiment, an experimentally determined final parameter values K=9 and θ=0.25 is chosen and herein the information propagation after k determined steps is stopped, that is after path length of 9 is achieved. Further, the convolution parameter θ, herein referred as dampening factor, is to propagate less information between nodes that have longer paths (or at a distance). Based on the convolution parameters as described above the inferred associations is obtained by running GCAS on the initial heterogeneous network with these parameters.

As described before, the first-order approximation of the spectral convolution is used in the information propagation model in the present embodiment. In conventional research, a GCN (Graph Convolutional Network), which is a convolutional neural network based on spectral graph convolution, was proposed for semi-supervised node classification in graphs. Each layer of the GCN neural network is based on the same first order approximation of the spectral graph convolution together with point-wise non-linearity. Two-layer GCN was used for node classification tasks in citation and knowledge networks in the conventional research. GCAS shares resemblance to GCN in the sense that both approaches are based on spectral graph convolution. However, the cross entropy based error model in GCN makes it more suitable for inferring the cumulative association of a sufficiently large set of related nodes in the graph to the remaining nodes rather than inferring individual pair-wise associations. Furthermore, with the observation that convolution with the $K^{th}$ order neighborhood require deeper networks in GCN which leads to increase in the number of parameters and may lead to over fitting. On the other hand, the GCAS performs direct spectral convolution (using the first order approximation) successively with the chosen filter parameters to efficiently propagate the signal to the $k^{th}$ order neighborhood of a node. This allows efficient estimation of long range associations from each single node to its $K^{th}$ order neighborhood for large K values.

At 408, the method includes creating a Heterogeneous Association Network for Rare Diseases (HANRD) by adding the inferred associations to the initial heterogeneous network. The initial heterogeneous network of curated associations is then augmented with the inferred associations obtained by performing GCAS on this initial heterogeneous network being constructed. These inferred associations together with the ontological and curated associations form the heterogeneous network HANRD (see FIG. 2). The constructed HANRD is used for the gene prioritization step.

At 410, the method includes generating a prioritized set of genes for an input query being received in the HANRD. The input disease query includes a plurality of phenotypes corresponding to a clinical case. The prioritized set of genes is generated by sorting cumulative association score between each of the phenotype from the plurality of phenotypes and associated genes for each of the phenotype in the HANRD. For a set of input containing plurality of phenotypes, their gene neighbors in HANRD is ranked based on their cumulative association score with respect to the input phenotypes, where the cumulative score is given by the sum of the association scores with individual phenotypes.

An example of experimental results to evaluate the performance of disclosed HANRD vis-à-vis conventional method for gene prioritization, for example, for a clinical case is discussed below with reference to FIGS. 5-7.

Validation and Results:

The present disclosure and associated embodiments thereof provides method for constructing the HANRD to solve specific task of phenotype-driven rare disease gene prioritization wherein the input is a set of phenotypes from clinical cases and the output a ranked list of possible causal genes. HANRD's application was validated for the specific task using a dataset of solved rare disease clinical cases reported in recent publications. The dataset of solved rare disease includes a list of clinical phenotype terms for each case along with the diagnosed disease(s) and the corresponding causal gene(s). The clinical cases from known literature was used with enforced HPO coding of the phenotypic terms of the clinical cases using the PhenoTips tool. For cases with no access to HPO codes were manually assigned for each clinical phenotypic terms using a verbatim search via the HPO browser interface. For cases, apart from those assigned by PhenoTips tool, each phenotypic term were assigned HPO codes manually. Further, any other disease term mentioned in the phenotype description without the HPO codes were ignored. These HPO IDs representing the clinical phenotype of a case served as input query to the HANRD. For each HPO ID, HANRD was queried resulting in a ranked list of genes. After iterating over all input HPOs, a single list of ranked genes was obtained. Rank of the known causal gene was checked for its presence in this list.

In the present experiment, performance using HANRD for the 230 solved cases was compared with that of Orphamizer. Since HANRD uses Orphanet data, Orphamizer was chosen instead of Phenomizer. Herein, each case consists of the plurality of phenotypes corresponding to a clinical case, the plurality of phenotypes terms were represented by HPO IDs while the corresponding output was a ranked list of associated genes to the each of the plurality of phenotypes. Further, cumulative frequency distribution of the number of input phenotype-genotype pairs—was considered for different Top-k values. For different Top-k values, the percentage of phenotype-gene pairs where the causal gene appeared within the Top-k of the ranked list of genes for the phenotype was measured.

One of the convention method used for comparison in the present example is BiRW algorithm. The BiRW algorithm has previously shown to outperform other state-of-the-art network inference algorithms. An experiment was conducted by the present disclosure and embodiments thereof to compare the performance of BiRW and GCAS for inferring novel associations. In the conventional BiRW implementation the nodes represent genes and disease phenotypes, while the edges are phenotype-gene associations from OMIM (Online Mendelian Inheritance in Man) and National Center for Biotechnology Information, National Library of Medicine, protein-protein interactions (PPI) and phenotype-phenotype associations. In order to perform the experiment, the proposed systems and methods constructed an instance of HANRD herein referred as $HANRD_{trunc}$ consisting of only phenotype and gene nodes and only the curated associations involving them. This was done by removing all intermediate disease(s) and pathway nodes in HANRD and introducing direct connections between the genes and phenotypes nodes. Parameters for BiRW were assigned the same optimal values as in the original conventional implementation. BiRW requires OMIM disease phenotypes as input, using the corresponding OMIM IDs. On the other hand, GCAS has been designed to take HPO phenotypes (HPO IDs) as input. Hence, the BiRW implementation was modified to handle HPO IDs as input. The modified implementation is referred to as $BiRW_{mod}$.

For comparison, the systems and methods of the present disclosure performed 10-fold cross validation by running both GCAS and $BiRW_{mod}$ on $HANRD_{trunc}$. In each fold, 10% (670) phenotype-gene links were removed from $HANRD_{trunc}$ at random. Both methods were run on remaining network of HANRD to augment it with inferred associations. The removed phenotype-gene associations form the $HANRD_{trunc}$ were used as test data. The $AUC_N$ (Area Under the Curve) value of the ROC (Receiver Operating Characteristic) curve was computed separately for each test phenotype. The ROC score was derived based on the ranks of the target genes associated with the phenotype among all its gene neighbors in the network. For $AUC_N$, the number of false positives are limited to be at most N. The average $AUC_N$ value was computed within a fold. Although removal of several existing network edges can affect the overall performance and thereby results in lower AUC values, these values can nevertheless be used for comparison of the two algorithms/techniques.

The present disclosure also compared GCAS with BiRW in the specific context of these 230 real-world cases. Both GCAS and the modified BiRW ($BiRW_{mod}$) were run on $HANRD_{trunc}$ for the 230 cases. For each of the 230 cases, an association pair for each phenotype and causal gene(s) was built. Since $BiRW_{mod}$ produces a separate ranked list of genes for each phenotype term of the input phenotype list, each input phenotype was analyzed separately. The results of the aforementioned comparison experimentation is depicted in the form of graphs as shown in FIGS. 5-7.

Figure 5:
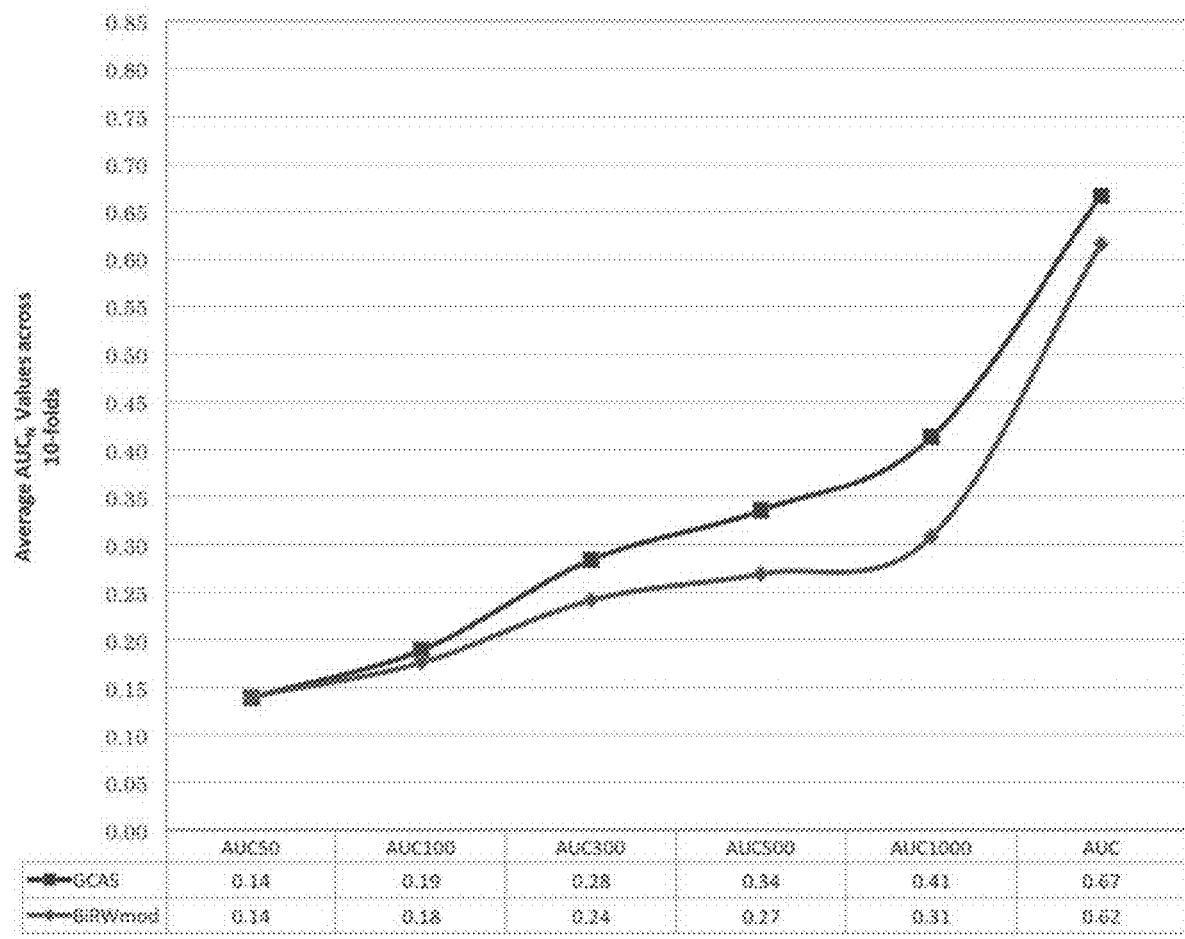
FIG. 5 depicts the comparison of GCAS with $BiRW_{mod}$, based on AUC value for 10-fold cross validation, in accordance with some embodiments of the present disclosure.

FIG. 5 depicts the comparison of GCAS (proposed method by the present disclosure) with $BiRW_{mod}$, based on the 10-fold cross validation described above according to an embodiment of the present disclosure. More specifically, FIG. 5 depicts average $AUC_N$ with N=50, 100, 300, 500, 1000 and the full AUC value for the 10-fold cross validation of GCAS and $BiRW_{mod}$. The $AUC_N$ values and the full AUC value averaged over all folds are shown in FIG. 5 for both $BiRW_{mod}$ and GCAS. As observed in FIG. 5, the plot shows marginally improved performance of GCAS over $BiRW_{mod}$ for larger Top-k. The technique BiRW explores domain specific short range connections in a network involving only genes and phenotypes. GCAS on the other hand explores both long range and short range connections in a domain-independent fashion. It is further observed in accordance with the present embodiments, in the present systems and methods associated thereof, the AUC values are shown only to compare the performance two of two algorithms (conventionally known and present method) and not merely to quantify the performance of any one algorithms in isolation.

Figure 6:
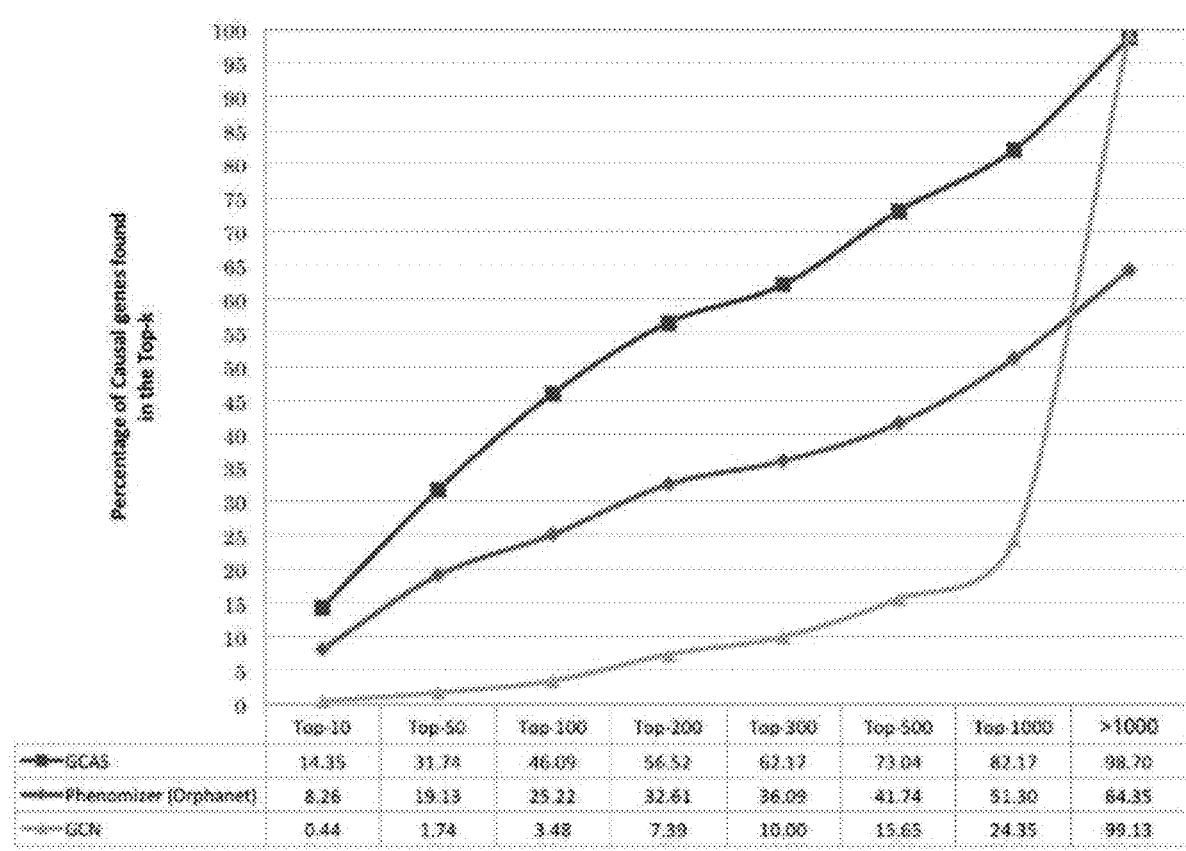
FIG. 6 depicts cumulative percentage of the 230 clinical cases for causal gene(s) appearing within the Top-k of the ranked list of genes using GCAS, Phenomizer (Orphanet) and GCN, in accordance with some embodiments of the present disclosure.

FIG. 6—shows comparison of CGAS, Phenomizer (Orphanet) and GCN. For different Top-k values, the percentage of cases where the causal gene(s) appeared within the Top-k of the ranked list of genes for the input set of phenotypes was plotted. The Orphamizer output was ranked disease-wise, wherein a gene could occur in the list for more than one input phenotype associated with the disease. In such cases, the highest rank for the causal genes was assigned. As observed in the FIG. 6, CGAS captured causal gene(s) for more than 31% of the cases in Top-50 and more than 56% of the cases in Top-200, when compared with Orphamizer which got 19 and 32% respectively and with GNC which got approximately 4% and 8% respectively.

Figure 7:
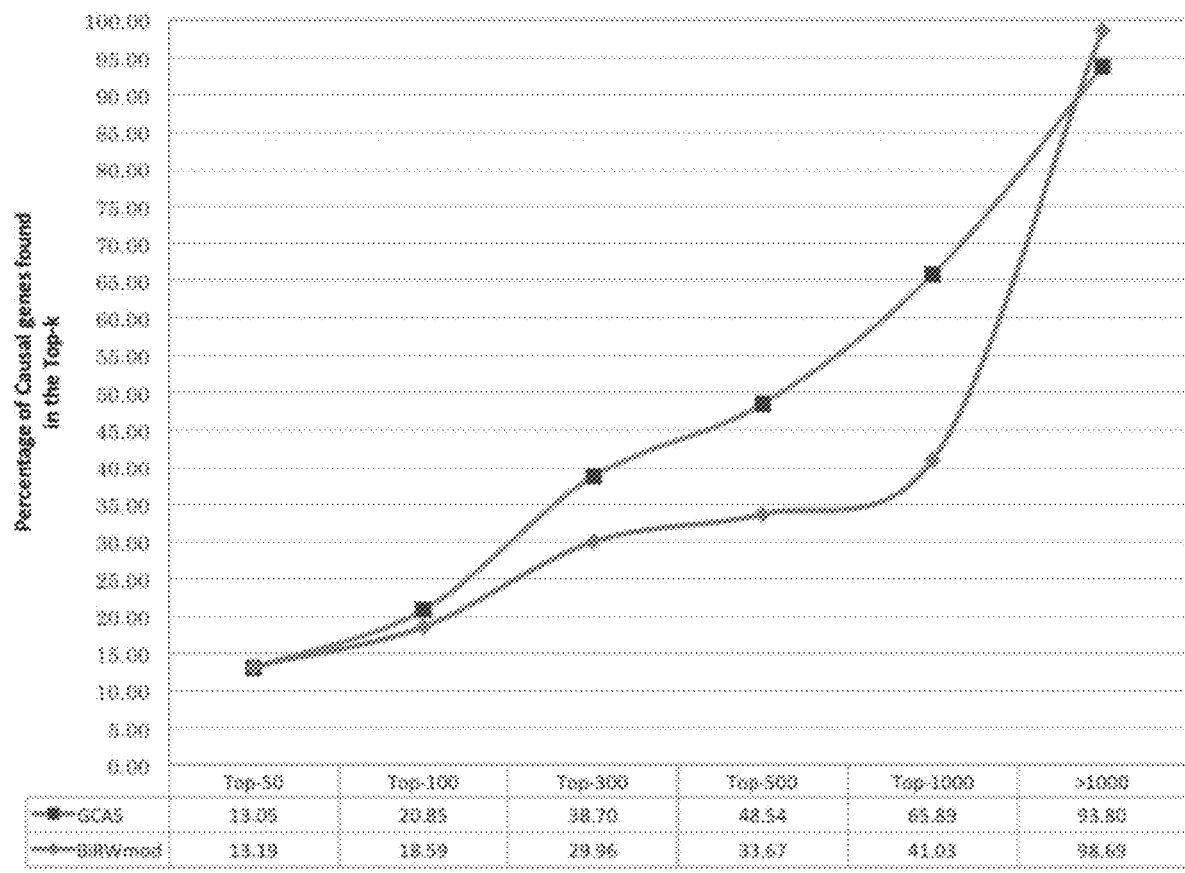
FIG. 7 depicts the comparison of GCAS with $BiRW_{mod}$, based on the 10-fold cross validation, in accordance with some embodiments of the present disclosure.

FIG. 7, with reference to FIGS. 1 through 4, depicts comparison of GCAS and $BiRW_{mod}$ for all the phenotype-gene pairs derived from the clinical cases according to an embodiment of the present disclosure. More specifically, FIG. 7 depicts cumulative distribution of the number of phenotype-gene pairs whose genes appear in the Top-k of the ranked list of its phenotype. In other words, FIG. 7 depicts cumulative percentage of all the phenotype-gene associations from the 230 clinical cases that appeared within the Top-k of the ranked gene list. The candidate methods are GCAS and $BiRW_{mod}$. FIG. 7, with reference to FIGS. 1 through 4, depicts distribution after excluding from the Top-k calculation those phenotype-gene pairs that are already linked in $HANRD_{trunc}$ with non-zero association scores according to an embodiment of the present disclosure.

The embodiments of the present disclosure provide a phenotype-driven approach for rare disease gene prioritization consisting of a heterogeneous network HANRD as well as a spectral graph convolution algorithm GCAS for inferring pairwise associations. As mentioned in the above present disclosure, the HANRD was built using ontological and curated associations supplemented by inferred associations. The validation results on rare disease clinical cases show improved performance when compared with to other state-of-the-art tools. As observed in FIGS. 5-7, when the phenotypes associated with the rare disease clinical cases were presented as input, the causal genes were captured within Top-50 for more than 31% of the cases and within Top-200 for more than 56% of the cases.

Also, as observed in the FIGS. 5-7 GCAS shows better recall than BiRW over a large Top-k range for the clinical cases. The recall performance of GCAS and BiRW are similar for small Top-k (Top-50). BiRW relies on a rigid network structure and it explores short range connections between entities. As a result, BiRW exhibits comparable precision (smaller Top-k) for a small subset of clinical cases. On the other hand, exploring only rigid structures with short range connections result in lower recall for BiRW for most other cases. Since GCAS explores both short-range and long-range connections, it is able to achieve a better balance of precision and recall. Computing long-range associations suffers from noise since the neighborhood expands considerably for increasing k. As a result, causal genes may appear only in a larger Top-k range. Nevertheless, good recall with reasonably large Top-k can still significantly help in identifying causal genes in rare disease clinical cases, especially when the ranked gene list output is combined with other similar lists arising from say genotyping (WES or WGS) experiments. Though the candidate genes could have lower rank in a list in isolation, combining its support from all ranked lists can produce a list of significantly higher quality than any of the individual lists and thereby help in efficient identification of the causal gene(s).

Furthermore, the BiRW approach explores domain specific and rigid sub-structures, that is, circular bigraphs consisting of only genes and phenotypes in the network for inferring novel associations. On the other hand, GCAS as described in the present embodiments uses a domain-independent approach and explores both short range and long range connections to infer novel associations (i.e., inferred associations) as described in the preceding paragraphs. Thus, the GCAS is better suited for adapting to other domains. Further, existing approaches usually view ontological associations as distinct from ontological pairwise associations. However, HANRD includes both types of associations in the same heterogeneous network while achieving superior performance.

The embodiments enable the present disclosure to combine pairwise ontological and curated associations into a single heterogeneous association network. The systems and methods of the present disclosure describes developing an information propagation algorithm GCAS (Graph Convolution-based Association Scoring) for performing information propagation on the initial ontological and curated association network and infers novel binary associations between the entities of the network. These inferred associations are added to the aforementioned initial network, and the resulting network of ontological, curated and inferred associations is termed as HANRD for Heterogeneous Association Network for Rare Diseases. The present disclosure enables building the HANRD to solve the specific problem of phenotype-driven rare disease gene prioritization wherein the input is a set of phenotypes from clinical cases and the output a ranked list of possible causal genes. Further observations in aforementioned results and validation infers that the present embodiments improve causal gene identification in rare diseases. Further, the improved performance exhibited by the inferring algorithm GCAS suggests spectral graph convolution, or graph signal processing in general, as one of the improved approach for biomedical network analysis, as in case of present embodiments.

FIG. 8 is a block diagram of an exemplary computer system 801 for implementing embodiments consistent with the present disclosure. The computer system 801 may be implemented in alone or in combination of components of the system 102 (FIG. 1). Variations of computer system 801 may be used for implementing the devices included in this disclosure. Computer system 801 may comprise a central processing unit ("CPU" or "hardware processor") 802. The hardware processor 802 may comprise at least one data processor for executing program components for executing user- or system-generated requests. The processor may include specialized processing units such as integrated system (bus) controllers, memory management control units, floating point units, graphics processing units, digital signal processing units, etc. The processor may include a microprocessor, such as AMD Athlon™, Duron™ or Opteron™, ARM's application, embedded or secure processors, IBM PowerPC™, Intel's Core, Itanium™, Xeon™, Celeron™ or other line of processors, etc. The processor 802 may be implemented using mainframe, distributed processor, multi-core, parallel, grid, or other architectures. Some embodiments may utilize embedded technologies like application specific integrated circuits (ASICs), digital signal processors (DSPs), Field Programmable Gate Arrays (FPGAs), etc.

Processor 802 may be disposed in communication with one or more input/output (I/O) devices via I/O interface 803. The I/O interface 803 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.11 a/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 803, the computer system 801 may communicate with one or more I/O devices. For example, the input device 804 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc.

Output device 805 may be a printer, fax machine, video display (e.g., cathode ray tube (CRT), liquid crystal display (LCD), light-emitting diode (LED), plasma, or the like), audio speaker, etc. In some embodiments, a transceiver (Tx/Rx) 806 may be disposed in connection with the processor 802. The transceiver may facilitate various types of wireless transmission or reception. For example, the transceiver may include an antenna operatively connected to a transceiver chip (e.g., Texas Instruments WiLink WL1283, Broadcom BCM4750IUB8, Infineon Technologies X-Gold 618-PMB9800, or the like), providing IEEE 802.11a/b/g/n, Bluetooth, FM, global positioning system (GPS), 2G/3G HSDPA/HSUPA communications, etc.

In some embodiments, the processor 802 may be disposed in communication with a communication network 808 via a network interface 807. The network interface 807 may communicate with the communication network 808. The network interface may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 908 may include, without limitation, a direct interconnection, local area network (LAN), wide area network (WAN), wireless network (e.g., using Wireless Application Protocol), the Internet, etc. Using the network interface 807 and the communication network 808, the computer system 801 may communicate with devices 809 and 810. These devices may include, without limitation, personal computer(s), server(s), fax machines, printers, scanners, various mobile devices such as cellular telephones, smartphones (e.g., Apple iPhone, Blackberry, Android-based phones, etc.), tablet computers, eBook readers (Amazon Kindle, Nook, etc.), laptop computers, notebooks, gaming consoles (Microsoft Xbox, Nintendo DS, Sony PlayStation, etc.), or the like. In some embodiments, the computer system 801 may itself embody one or more of these devices.

In some embodiments, the processor 802 may be disposed in communication with one or more memory devices (e.g., RAM 813, ROM 814, etc.) via a storage interface 812. The storage interface may connect to memory devices including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc. Variations of memory devices may be used for implementing, for example, any databases utilized in this disclosure.

The memory devices may store a collection of program or database components, including, without limitation, an operating system 816, user interface 817, user/application data 818 (e.g., any data variables or data records discussed in this disclosure), etc. The operating system 816 may facilitate resource management and operation of the computer system 801. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like. User interface 817 may facilitate display, execution, interaction, manipulation, or operation of program components through textual or graphical facilities. For example, user interfaces may provide computer interaction interface elements on a display system operatively connected to the computer system 801, such as cursors, icons, check boxes, menus, scrollers, windows, widgets, etc. Graphical user interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, computer system 801 may store user/application data 818, such as the data, variables, records, etc. as described in this disclosure. Such databases may be implemented as fault-tolerant, relational, scalable, secure databases such as Oracle or Sybase. Alternatively, such databases may be implemented using standardized data structures, such as an array, hash, linked list, structured text file (e.g., XML), table, or as object-oriented databases (e.g., using ObjectStore, Poet, Zope, etc.). Such databases may be consolidated or distributed, sometimes among the various computer systems discussed above in this disclosure. It is to be understood that the structure and operation of any computer or database component may be combined, consolidated, or distributed in any working combination.

Additionally, in some embodiments, the server, messaging and instructions transmitted or received may emanate from hardware, including operating system, and program code (i.e., application code) residing in a cloud implementation. Further, it should be noted that one or more of the systems and methods provided herein may be suitable for cloud-based implementation. For example, in some embodiments, some or all of the data used in the disclosed methods may be sourced from or stored on any cloud computing platform.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims (when included in the specification), the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments.

We claim:

1. A hardware processor-implemented method comprising:
　as implemented by one or more hardware processors configured by instructions stored in a memory,
　obtaining a set of entities for human rare diseases from one or more sources, the set of entities comprising rare diseases, genes, phenotypes for rare diseases and biological pathways (402);
　constructing an initial heterogeneous network using each of an entity from the set of entities as a node and associations between a plurality of entity pairs as symmetric weighted edges forming pair-wise ontological associations and curated associations (404) wherein the curated associations comprise disease-gene associations, gene-gene associations, and phenotype-disease associations formed using the weights assigned to each of a plurality of pair edges from the one or more sources and ontological associations includes: determining a pair-wise association score based on a Lin similarity of the defined ontological relationships between the phenotypes; and forming phenotype-phenotype edges for each of the phenotypes and assigning the determined pair-wise association score to obtain the pair-wise ontological associations, wherein forming associations of the biological pathways comprises:
linking each gene present in a biological pathway with a corresponding pathway node with another gene based on an assigned weight;
applying a Graph Convolution-based Association Scoring (GCAS) to the initial heterogeneous network for deriving inferred associations for the plurality of entity pairs (406), wherein deriving the inferred associations comprises determining information propagated between neighborhood nodes of each of the plurality of entity pairs in the initial heterogeneous network using the curated associations and based on the convolution parameters comprising convolution operation (C), dampening factor (θ) and convolution depth (K);
determining association scores, for each of the plurality of entity pairs having no direct links, based on the determined information propagated to obtain the pairwise association score matrix; and
inferring associations between each of the plurality of entities based on the pairwise association score matrix to obtain the inferred associations;
creating a Heterogeneous Association Network for Rare Diseases (HANRD) by adding the inferred associations to the initial heterogeneous network (408), wherein the initial heterogeneous network of the curated associations is augmented with the inferred associations obtained by performing the GCAS on the initial heterogeneous network; and
generating a prioritized set of genes for an input query being received in the HANRD, the input query comprising a plurality of phenotypes corresponding to a clinical case (410), and wherein generating the prioritized set of genes comprises sorting cumulative association score between each of the phenotype from the plurality of phenotypes and associated genes for each of the phenotype in the HANRD wherein the cumulative association score is sum of association scores for each of the plurality of phenotypes, and wherein the association score is based on the gene neighbors of each of the plurality of phenotypes, wherein representing a clinical phenotype of the clinical case served as the input query results in a ranked list of causal genes and wherein the causal genes are ranked based on the cumulative association score in the HANRD.

2. The method of claim 1, wherein the one or more sources comprise Medical Subject Headings (MeSH), Orphanet, Human Phenotype Ontology (HPO), HUGO Gene Nomenclature Committee and Wiki Pathways.

3. The method of claim 1, wherein the disease entity is derived from the one or more sources, and wherein the disease entity is derived from an Orphanet record comprising rare disease name and synonyms, descriptions of the rare disease, phenotypes, association strength, genes of the rare disease and MeSH mappings associated with the rare disease.

4. The method of claim 1, wherein the information propagated is given by an equation:

$$C_t(x) = \theta^t \hat{A}^t x$$

wherein $C_t(x)$ is convolution operation for information propagated to $t^{th}$ order of neighborhood of network nodes by performing t consecutive applications in the convolution operation (C), wherein
$\theta^t = \Pi_{i=1}^{t} \theta_i$ and $\theta_i$ is the dampening factor for the $i^{th}$ convolution application, and wherein
$\hat{A}^t x$ is a first order approximation based on Chebyshev polynomial approximation.

5. The method of claim 1, wherein the pairwise association score matrix is represented by an equation:

$$S = \Sigma_{t=1}^{K} C_t(I_n),$$

wherein S is the pairwise association score matrix,
wherein $C_t(I_n) = \theta^{t-2} \hat{A}^t I_n$, for t≥2,
and wherein $\hat{A}^t I_n$ is a first order approximation based on Chebyshev polynomial approximation and n=number of nodes in the network.

6. A system comprising:
a memory storing instructions;
one or more hardware processors coupled to the memory, wherein the one or more hardware processors are configured by the instructions to:
obtain a set of entities for human rare diseases from one or more sources, the set of entities comprising rare diseases, genes, phenotypes for rare diseases and biological pathways;
construct an initial heterogeneous network using each of an entity from the set of entities as a node and associations between a plurality of entity pairs as symmetric weighted edges forming pair-wise ontological associations and curated associations wherein the curated associations comprise disease-gene associations, gene-gene associations, and phenotype-disease associations formed using the weights assigned to each of a plurality of pair edges from the one or more sources and ontological associations includes:
determining a pair-wise association score based on a Lin similarity of the defined ontological relationships between the phenotypes; and forming phenotype-phenotype edges for each of the phenotypes and assigning the determined pair-wise association score to obtain the pair-wise ontological associations, wherein forming associations of the biological pathways comprises:
linking each gene present in a biological pathway with a corresponding pathway node with another gene based on an assigned weight;
applying a Graph Convolution-based Association Scoring (GCAS) to the initial heterogeneous network to derive inferred associations for the plurality of entity pairs, wherein deriving the inferred associations comprises: determining information propagated between neighborhood nodes of each of the plurality of entity pairs in the initial heterogeneous network using the curated associations and based on the convolution parameters comprising convolution operation (C), dampening factor (θ) and convolution depth (K);
determining association scores, for each of the plurality of entity pairs having no direct links, based on the determined information propagated to obtain the pairwise association score matrix; and
inferring associations between each of the plurality of entities based on the pairwise association score matrix to obtain the inferred associations;
creating a Heterogeneous Association Network for Rare Diseases (HANRD) by adding the inferred associations to the initial heterogeneous network, wherein the initial heterogeneous network of the curated associations is augmented with the inferred associations obtained by performing the GCAS on the initial heterogeneous network; and generating a prioritized set of genes for an input query being received in the HANRD, the input query comprising a plurality of phenotypes corresponding to a clinical case, and wherein generating the prioritized set of genes comprises sorting cumulative association score between each of the phenotype from the plurality of phenotypes and associated genes for each of the phenotype in the HANRD wherein the cumulative association score is sum of association scores for each of the plurality of phenotypes, and wherein the association score is based on the gene neighbors of each of the plurality of phenotypes, wherein representing a clinical phenotype of the clinical case served as the input query results in a ranked list of causal genes and wherein the causal genes are ranked based on the cumulative association score in the HANRD.

7. The system of claim 6, wherein the information propagated is given by equation:

$$C_t(x) = \theta^t \hat{A}^t x$$

wherein $C_t(x)$ is convolution operation for information propagated to $t^{th}$ order of neighborhood of network nodes by performing t consecutive applications in the convolution operation (C), wherein
$\theta^t = \Pi_{i=1}^t \theta_i$ and $\theta_i$ is the dampening factor for the $i^{th}$ convolution application, and wherein
$\hat{A}^t x$ is a first order approximation based on Chebyshev polynomial approximation.

8. The system of claim 6, wherein the pairwise association score matrix is represented by the equation:

$$S = \Sigma_{t=1}^K C_t(I_n),$$

wherein S is the pairwise association score matrix,
wherein $C_t(I_n) = \theta^{t-2} \hat{A}^t I_n$, for $t \geq 2$,
and wherein $\hat{A}^t I_n$ is a first order approximation based on Chebyshev polynomial approximation and n=number of nodes in the network.

9. A non-transitory computer-readable medium having embodied thereon a computer program for executing a method gene prioritization, the method comprising:
obtaining a set of entities for human rare diseases from one or more sources, the set of entities comprising rare diseases, genes, phenotypes for rare diseases and biological pathways (402);
constructing an initial heterogeneous network using each of an entity from the set of entities as a node and associations between a plurality of entity pairs as symmetric weighted edges forming pair-wise ontological associations and curated associations (404) wherein the curated associations comprise disease-gene associations, gene-gene associations, and phenotype-disease associations formed using the weights assigned to each of a plurality of pair edges from the one or more sources and ontological associations includes: determining a pair-wise association score based on a Lin similarity of the defined ontological relationships between the phenotypes; and forming phenotype-phenotype edges for each of the phenotypes and assigning the determined pair-wise association score to obtain the pair-wise ontological associations, wherein forming associations of the biological pathways comprises:
linking each gene present in a biological pathway with a corresponding pathway node with another gene based on an assigned weight;
applying a Graph Convolution-based Association Scoring (GCAS) to the initial heterogeneous network for deriving inferred associations for the plurality of entity pairs (406), wherein deriving the inferred associations comprises: determining information propagated between neighborhood nodes of each of the plurality of entity pairs in the initial heterogeneous network using the curated associations and based on the convolution parameters comprising convolution operation (C), dampening factor (θ) and convolution depth (K);
determining association scores, for each of the plurality of entity pairs having no direct links, based on the determined information propagated to obtain the pairwise association score matrix; and
inferring associations between each of the plurality of entities based on the pairwise association score matrix to obtain the inferred associations;
creating a Heterogeneous Association Network for Rare Diseases (HANRD) by adding the inferred associations to the initial heterogeneous network (408), wherein the initial heterogeneous network of the curated associations is augmented with the inferred associations obtained by performing the GCAS on the initial heterogeneous network; and
generating a prioritized set of genes for an input query being received in the HANRD, the input query comprising a plurality of phenotypes corresponding to a clinical case (410), and wherein generating the prioritized set of genes comprises sorting cumulative association score between each of the phenotype from the plurality of phenotypes and associated genes for each of the phenotype in the HANRD wherein the cumulative association score is sum of association scores for each of the plurality of phenotypes, and wherein the association score is based on the gene neighbors of each of the plurality of phenotypes, wherein representing a clinical phenotype of the clinical case served as the input query results in a ranked list of casual causal genes and wherein the casual causal genes are ranked based on the cumulative association score in the HANRD.

* * * * *